United States Patent
Readhead et al.

(10) Patent No.: US 7,294,755 B1
(45) Date of Patent: Nov. 13, 2007

(54) GENETIC MODIFICATION OF MALE GERM CELLS FOR GENERATION OF TRANSGENIC SPECIES AND GENETIC THERAPIES

(75) Inventors: Carol W. Readhead, Pasadena, CA (US); Robert Winston, London (GB)

(73) Assignees: Cedars-Sinai Medical Center, Los Angeles, CA (US); Imperial College Innovations Ltd., London (GB)

(*) Notice: Subject to any disclaimer, the term of this patent is extended or adjusted under 35 U.S.C. 154(b) by 0 days.

(21) Appl. No.: 09/570,357

(22) Filed: May 12, 2000

Related U.S. Application Data

(63) Continuation-in-part of application No. 09/311,599, filed on May 13, 1999, now Pat. No. 6,734,338, which is a continuation-in-part of application No. 09/191,920, filed on Nov. 13, 1998, now Pat. No. 6,316,692.

(60) Provisional application No. 60/065,825, filed on Nov. 14, 1997.

(51) Int. Cl.
C12N 15/00 (2006.01)
(52) U.S. Cl. .......................................... 800/22; 800/23
(58) Field of Classification Search .................. 800/18, 800/23; 435/320.1
See application file for complete search history.

(56) References Cited

U.S. PATENT DOCUMENTS

| | | | |
|---|---|---|---|
| 4,663,281 A | 5/1987 | Gillies et al. | |
| 4,762,701 A | 8/1988 | Horan et al. | |
| 4,870,009 A | 9/1989 | Evans et al. | |
| 4,959,313 A | 9/1990 | Taketo | |
| 4,978,332 A | 12/1990 | Luck et al. | |
| 5,175,384 A | 12/1992 | Krimpenfort et al. | |
| 5,206,143 A | 4/1993 | Horan et al. | |
| 5,358,711 A | 10/1994 | May et al. | |
| 5,375,606 A | 12/1994 | Slezak et al. | |
| 5,422,266 A | 6/1995 | Cormier et al. | |
| 5,430,057 A | 7/1995 | Anderson et al. | |
| 5,434,340 A | 7/1995 | Krimpenfort et al. | |
| 5,491,084 A | 2/1996 | Chalfie et al. | |
| 5,521,291 A | 5/1996 | Curiel et al. | |
| 5,532,143 A | 7/1996 | Grosveld et al. | |
| 5,543,291 A | 8/1996 | Keyomarsi et al. | |
| 5,547,932 A | 8/1996 | Curiel et al. | |
| 5,556,954 A | 9/1996 | Burn et al. | |
| 5,559,148 A | 9/1996 | Anderson et al. | |
| 5,591,625 A | 1/1997 | Gerson et al. | |
| 5,591,669 A | 1/1997 | Krimpenfort et al. | |
| 5,610,053 A | 3/1997 | Chung et al. | |
| 5,625,048 A | 4/1997 | Tsien et al. | |
| 5,639,618 A | 6/1997 | Gay | |
| 5,643,741 A | 7/1997 | Tsukamoto et al. | |
| 5,650,135 A | 7/1997 | Contag et al. | |
| 5,665,557 A | 9/1997 | Murray et al. | |
| 5,670,372 A | 9/1997 | Hogan | |
| 5,686,279 A * | 11/1997 | Finer | 435/172.3 |
| 5,750,376 A | 5/1998 | Weiss et al. | |
| 5,767,258 A | 6/1998 | Sidransky | |
| 5,777,079 A | 7/1998 | Tsien et al. | |
| 5,821,234 A | 10/1998 | Dzau | |
| 5,840,478 A | 11/1998 | Patterson et al. | |
| 5,858,354 A * | 1/1999 | Brinster | 424/93.7 |
| 6,271,436 B1 * | 8/2001 | Piedrahita | 800/21 |

FOREIGN PATENT DOCUMENTS

| | | |
|---|---|---|
| EP | 0 867 114 A1 | 9/1998 |
| WO | WO 90/08192 | 7/1990 |
| WO | WO 92/03459 | 3/1992 |

(Continued)

OTHER PUBLICATIONS

Maione et al., Sperm-mediated gene transfer in mice, 1998, Molecular Reproduction and Development, vol. 50, pp. 406-409.*
Sato et al., Testis-mediated gene transfer (TMGT) in mice: Successful transmission of introduced DNA from f0 to F2 generations, 1999, TRANSGENICS, vol. 3, pp. 11-22.*
Lavitrano et al., Sperm-mediated gene transfer: Production of pigs transgenic for a human regulator of complement activation, 1997, Transplantation Proceedings, vol. 29, pp. 3508-3509.*
Li et al. (Proceedings of International Conference on Animal Biotechnology, Supplement, 1997, pp. 30-34).*

(Continued)

*Primary Examiner*—Celine Qian
(74) *Attorney, Agent, or Firm*—C. G. Mersereau; Nikolai & Mersereau, P.A.

(57) ABSTRACT

Disclosed is an in vivo method of incorporating exogenous genetic material into the genome of a vertebrate, which involves administering to a male vertebrate's testis a gene delivery mixture comprising a viral vector, such as a retroviral vector, to deliver a polynucleotide encoding a desired trait or product. Also disclosed is an in vitro method of incorporating exogenous genetic material into the genome of a vertebrate, in which germ cells are obtained from a donor male vertebrate and are genetically modified in vitro, before being transferred to a recipient male vertebrate. After the transfer, the male vertebrate bearing the genetically modified germ cells is bred with a female vertebrate such that a transgenic progeny is produced that carries the polynucleotide in its genome. Also disclosed are non-human transgenic vertebrates produced in accordance with the method, including transgenic progeny. A transgenic cell derived from the transgenic vertebrate is also disclosed, being a germ cell, such as a spermatozoan or ovum, a precursor cell of either of these, or a somatic cell. A method of producing a non-human transgenic vertebrate animal line comprising native germ cells carrying in their genome at least one xenogeneic polynucleotide is disclosed, as is vertebrate semen containing the transgenic male germ cells useful in practicing the method.

21 Claims, 3 Drawing Sheets

FOREIGN PATENT DOCUMENTS

| WO | WO 93/11228 | 6/1993 |
| --- | --- | --- |
| WO | WO 95/02041 | 1/1995 |
| WO | WO 99/25863 A1 | 5/1999 |
| WO | WO99/38991 * | 8/1999 |
| WO | WO 99/40213 A1 | 8/1999 |
| WO | WO 00/29601 A1 | 5/2000 |
| WO | WO 00/29602 A1 | 5/2000 |

OTHER PUBLICATIONS

XP-000942592, Chang, Kyu-Tae et al., Production of Transfenic Rats and Mice by the Testis-Mediated Gene Transfer, *Journal of Reproduction and Development*, vol. 45, No. 1, pp. 29-36 (1999).
Annex to Form PCT/ISA/206 Communication Relating to the Results of the Partial International Search mailed Nov. 24, 2000.
Russell et al, Cache River Press, *Histological and Histopathological Evaluation of the Testis*, Clearwater, FI34620, pp. 1-40.
Western and Sinclair, Journal of Experimental Zoology, *Sex, Genes, and Heat: Triggers of Diversity*, vol. 290, (2001), pp. 624-631.
E. J. Slijper, KS Norris, Ed. University of California Press, Berkeley, CA, *Functional Morphology of the Reproductive System in Cetacea* In: Whales, Dolphins and Porpoises, pp. 278.
Avarbock, Mary R., et al., Reconstitution of spermatogenesis from frozen spermatogonial stem cells, *Nature Medicine*, vol. 2, No. 6, pp. 693-696, (Jun. 1996).
Baranov, V. S., et al., The possibility of the incorporation of macromolecules, including exogenous DNA, into the germ cells of male mice. The liposome method and Ca-P coprecipitation method, *Tsitol Genet*, vol. 24,No. 2,pp. 52-55 (Mar. 1990), Abstract Only.
Brinstiel, Max L., et al. Dangerous Liaisons: Spermatozoa as Natural Vectors for Foreign DNA?, *Cell*, vol. 57, pp. 701-702, (1989).
Blanchard, K.. T. et al., *Adenovirus-mediated gene transfer to rat testis in vivio*, Biol Reprod (Feb. 1997); 56(2):495-500.
Brinster, Ralph L., et al., No Simple Solution for Making Transgenic Mice, *Cell*, vol. 59, pp. 239-241, Oct. 20, 1989.
Brinster, Ralph L. et al., Avarbock, Germline transmission of donor haplotype following spermatogonial transplantation, *Proc. Natl. Acad. Sci. USA*, vol. 91, pp. 22303-22307, (Nov. 1994) Developmental Biology.
Brinster, Ralph L. et al., Spermatogenesis following male germ-cell transplantation, *Proc. Natl. Acad. Sci USA*, vol. 91, pp. 11298-11302, (Nov. 1994), Developmental Biology.
Chen, Shu-Hsia et al., Gene therapy for brain tumors: Regression of experimental gliomas by adenovirus-mediated gene transfer in vivo, *Proc. Natl. Acad. Sci. USA*, vol. 91, pp. 3054-3057, Apr. 1994.
Chung, J. H. et al., A 5' element of the chicken beta-globin domain serves as an insulator in human erythroid cells and protects against position effect in Drosophila, *Cell*, 74(3):505-14, Aug. 13, 1993, Abstract Only.
Chung, J. H. et al., Characterization of the chicken beta-globin insulator, *Proc. Natl. Acad. Sci. USA*. 94(2):575-80, Jan. 21, 1997, Abstract Only.
Clouthier, D. E. et al., Rat spermatogenesis in mouse testis, *Nature*, 381 (6581): 418-421 (May 30, 1996).
Curiel D. T., et al. Adenovirus enhancement of transferrin-polylysine-mediated gene delivery, *Proc. Natl. Acad. Sci-USA*, 88:8850-54(Oct. 1991).
Desdouets, C. et al, Cyclin A: function and expression during cell proliferation, *Prog Cell Cycle Res*, 1:115-23, 1995, Abstract Only.
Graberek & Gergely, Zero-length cross-linking procedure with the use of active esters, *Analyt. Biochem* 185: 131-135 (1990).
Hagstrom, K., et al., Fab-7 functions as a chromatin domain boundary to ensure proper segment specification by the Drosophila bithorax complex, *Genes Dev*, 10(24):3202-15, Dec. 15, 1996, Abstract Only.
Horiguchi-Yamada, J., et al., Changes of G1 cyclins, edk2, and cyclin A during the differentiation of HL60 cells induced by TPA, *Mol Cell Biochem*, 132(1):31-7, Mar. 16, 1994, Abstract Only.

Hovatta, Outi, et al., Cryopreservation of human ovarian tissue using dimethysulphoxide and propanediol-sucrose as cryoprotectants, *Human Reproduction*, vol. 11, No. 6, pp. 1268-1272, (1996).
Hovatta, Outi, et al., Pregnancy resulting from intracytoplasmic injection of spermatozoa from a frozen-thawed testicular biopsy specimen, *Human Reproduction*, vol. 11, No. 11, pp. 2472-2473, (1996).
Jiang, F-X et al., Male germ cell transplantation in rats: apparent syunchronization of spermatogenesis between host and donor seminiferous, epithelia, *International Journal of Andrology*, vol. 18, pp. 326-330 (1995).
Jiang, Fang-Xu et al., Different fate of primordial germ cells and gonocytes following transplantation, *APMIS*, vol. 106, pp. 58-63, (1998).
Johnson L, et al., Heterotoic transplantation as a model to study the regulation of spermatogenesis: some histomorphological considerations about sperm decline in man; *Contracept Fertil Sex* 1997 vol. 25(7-8), pp. 549-555, (1997).
Jones and Shenk, An adenovirus type 5 early gene function regulates expression of other early viral genes, *Proc. Natl. Acad. Sci. USA*, 76:(8)3665-3669 (1979).
Kang, M. J. et al., Cyclins and cyclin dependent kinases during cardiac development, *Mol Cells*, 7(3):360-6, (Jun. 30, 1997) Abstract Only.
Kim, Jin-Hoi et al., Development of a Positive method for Male stem Cell-Mediated Gene Transfer in Mouse and Pig, *Molecular Reproduction and Development*, vol. 46, No. 4, pp. 515-526, (1997).
Kim, V. Narry et al., Minimal requirement for a Lentivirus Vector Based on Human Immunodeficiency Virus Type 1, *Journal of Virology*, pp. 811-816, (Jan. 1998).
Langer, Robert S. et al., Tissue Engineering: The obstacles to building new organs from cells and synthetic polymers are daunting but surmountable The Challenges Ahead, *Scientific American*, pp. 86-89, Apr. 1999.
Lavitrano, Mariauisa et al., Sperm Cells as Vectors for Introducing foreign DNA Into Eggs: Genetic Transformation of Mice, *Cell*, vol. 57, pp. 717-723, (Jun. 2, 1989).
Mittereder et al., Evaluation of the concentration and bioactivity of adenovirus vectors for gene therapy, *J. Virology*, 70: 7498-7509 (1996).
Müller, C. et al., Cell cycle regulated transcription of the promoter of the human cyclin A1 gene, *Blood, Journal of the American Society of Hematology*, vol. 90, No. 10, Suppl 1 (Part 1 of 2) Nov. 15, 1997 Abstract 1404.
Müller, C. et al., *Cyclin A1 promoter is trans-activated by the c-myb proto-onco gene*, Proc. of the Amer. Assoc. for Cancer Res, vol. 39, Mar./Apr. 1998, Abstract 1742.
Müller, C.et al., SP1 Family Members Regulate Expression of the Tissue Specific Human Cyclin A1 Gene, *Blood Journal of the American society of Hematology*, Americ. Soc. Of Hemat.40th Annual Meeting, Dec. 4-8, 1998 Abstract 1534.
Müller, Carsten et al., Cloning of the cylin A1 Genomic Structure and Characterization of the Promoter Region, *The Journal of Biological Chemistry* vol. 276, No. 16, pp. 11220-11228, Apr. 16, 1998.
Muramatsu T. et al.., Foreign gene expression in the mouse testis by localized in vivo gene transfer, *Biochem Biophys Res commun*, 7;233(1):45-49 (Apr. 1997).
Nagano, M, et al., *Spermatogonial transplantation and reconstitution of donor cells spermatogenesis in recipient mice*, APMIS, 106, pp. 47-55, (1998).
Natio M, et al., Production of germline chimeric chickens, with high transmission rate of donor-derivied gametes, produced by transfer of primordial germ cells, *Molecular Reprod Dev.*, 39(2):153-161(Oct. 1994).
Naito M., et al., Donor primordial germ cell-derived offspring from recipient germline chimaeric chickens: absence of long-term immune rejection and effects on sex ratios, *Br Poult Sci*, 39(1):20-23 (Mar. 1998).
Naldini, Luigi et al., In Vivo Gene Delivery and Stable Transduction of Nondividing Cells by a Lentiviral Vector, *Science*, vol. 272, pp. 263-269, Apr. 12, 1996.

Ogawa, Takehiko et al., Transplantation of testis germinal cells into mouse seminiferous tubules, *Int. J. Dev. Biol.*, 41:222-122 (1997).

Ono T. et al., Transfer of male or female primordial germ cells of quail into chick embryonic gonads, *Exp Anim*, 45(4):347-352 (Oct. 1996).

Paterlini, P. et al., Cylin A expression in human hematological malignancies: a new marker of cell proliferation, *Cancer Res*, 53(2):235-8, (Jan. 15, 1993) Abstract Only.

Pedersen, Roger A., Cells for Medicine, *Embryonic Stem Cells for Medicine, Scientific American*, pp. 68-73 (Apr. 1999).

Perez-Cruet, M. J., et al., Adenovirus-Mediated Gene Therapy of Experimental gliomas, *Journal of Neuroscience Research*, vol. 39, pp. 506-511 (1994). meiotic cell cylces, Dev. Biol., 10:173(1):69-78, (Jan. 10, 1996).

Pikaart, Michael J., Loss of transcriptional activity of a transgene is accompanied by DNA methylation and histone deacetylation and is prevented by insulators, *Genes & Development*, 12:2852-2862, (1998).

Ravnik, S. E. et al., The developmentally restricted pattern of expression in the male germ line of a murine cylin A, cyclin A2, suggests roles in both mitotic and meiotic cell cycles, *Dev. Biol.*, 10:173(1):69-78, (Jan. 10, 1996). Abstract Only.

Ravnik, S. E. et al., Regulation of meiosis during mammalian spermatogenesis: the A-type cyclins and their associated cyclin-dependent kinases are differentially expressed in the germ-cell lineage, *Dev Bio*, 207(2):408-18 (Mar. 15, 1999). Abstract Only.

Russell, L.D. et al., Ultrastructural observations of spermatogenesis in mice resulting from transplantatin of mouse spermatogonia, *J. Androl.*, 17(6):603-614 (Nov. 1996).

Schmidt, Jerzy A. et al., Control of Erythroid differentiation. Possible Role of the Transferrin cycle, *Cell*, vol. 46, 41-51 (Jul. 4, 1986).

Schiedner, Gudrun, Genomic DNA transfer with a high-capacity adenovirus vector results in improved in vivo gene expression and decreased toxicity, *Nature Genetics*, vol. 18, pp. 180-183 (Feb. 1998).

Sweeney, Claire et al., A distinct cylin A is expressed in germ cells in the mouse, *Development*, vol. 122, pp. 53-64 (1996).

Wagner, Ernst, Transferrin-polycation conjugates as carriers for DNA uptake into cells, *Proc. Natl. Acad. Sci. USA*, vol. 87, pp. 3430-3414 (May 1990).

Wolffe, A. P., Packaging principle: how DNA methylation and histone acetylation control the transcriptional activity of chromatin, *J. Exp Zool*, 282(1-2):239-44 (Sep.-Oct. 1998). Abstract Only.

Yang, Rong et al., Characterization of a Second Human Cyclin A That is Highly Expressed in Testis and in Several Leukemic Cell Lines, *Cancer Research*, 57, pp. 913-920 (Mar. 1, 1997).

PCT International Search Report re PCT/US98/24238, International Filing Date: Nov. 13, 1998, Priority Date: Nov. 14, 1997.

XP-002099974, J09220039,"Introducing Extraneous Gene Sperm Ovum Produce Transgenic Animal Comprise Introducing Extraneous Gene Liposome Complex Through Testicular Ovary Artery Sperm Testicular Ovum Ovary", Abstract Only, no date.

Bucci, L. R. et al., *Effects of busulfan on murine spermatogenesis: cytotoxicity, sterility, sperm abnormalities, and dominant lethal mutations*, Research, vol. 176, pp. 259-268, (1987).

Kormano, M. et al., In vitro *contractility of rat seminiferous tubules following 400 R whole-body X-irradiation*, Strahlentherapie vol. 144, No. 6, pp. 713-718 (1972).

Oakberg, E. F., *Effects of radiation on the testis*, Handbook of Physiology, Endocrinology V, pp. 233-243, (date unknown).

Pont, Jorg et al., *Fertility after chemotherapy for testicular germ cell cancer*, Fertility and Sterility, vol. 68, No. 1, pp. 1-5, (Jul. 1997).

Boujrad, N. et al., *Evolution of somatic and germ cell populations after busulfan treatment in utero or neonatal cryptorchidism in the rat*, Andrologia, 27(4):223-8 (Jul.-Aug. 1995). Abstract Only.

Hasegawa, M., *Resistance of differentiating spermatogonia to radiation-induced apoptosis and loss in p53-deficient mice*, Radiat Res, 149(3):263:70, (Mar. 1998). Abstract Only.

Hopkinson, C. R., *The effect of local testicular irradiation on testicular histology and plasma hormone levels in the male rat*, Acta Endocrinol (Copenh), 87(2):413-23 (Feb. 1998). Abstract Only.

Jiang, F. X., Anat Embryol, *Behaviour of spermatogonia following recovery from busulfan treatment in the rat*, 198(1):53-61 (Jul. 1998). Abstract Only.

Kamtchouing, P., *Effect of continuous low-dose gamma-irradiation on rat Sertoli cell function*, Reprod Nutr Dev, 28(4B):1009-17 (1988). Abstract Only.

Kamtchouing, P., *Changes in androgen binding protein (ABP) production following continuous low dose gamma irradiation (IR) of adult rat*, Steroids, 52((4):349-50, (Oct. 1988). Abstract Only.

Kangasniemi, M., *Cellular regulation of basal and FSH-stimulated cyclic AMP production in irradiated rat testes*, 227(1):32-6 (May 1990). Abstract Only.

Kasuga, F., *The endocrine function of rat gonads with reduced number of germ cells following busulphan treatment*, Endocrinol Jpn, 33(1):105-15 (Feb. 1986). Abstract Only.

Linder, R. E., *Endpoints of spermatotoxicity in the rat after short duration exposures to fourteen reproductive toxicants*, Reprod Toxicol, 6(6):491-505 (1992). Abstract Only.

Pineau, C., *Assessment of testicular function after acute and chronic irradiation: further evidence for an influence of late spermatids on Sertoli cell function in the adult rat*, Endocrinology, 124(6):2720-8 (Jun. 1989). Abstract Only.

Pinon-Lataillade, G. et al., *Continuous gamma-irradiation of rates: dose-rate effect on loss and recovery of spermatogenesis*, Strahlentherapie, 161(7):421-6, (Jul. 1985). Abstract Only.

Pinon-Lataillade, G. et al., *Endocrinological and histological changes induced by continuous low dose gamma-irradiation of the rat testis*, Acta Endocrinol (Copenh), 109(4):558-62 (Aug. 1985). Abstract Only.

Pinon-Lataillade, G. et al., *Influence of germ cells upon Sertoli cells during continuous low-dose rate gamma-irradiation of adult rats*, Mol Cell Endocrinol, 58(1):51-63, (Jul. 1988). Abstract Only.

Pinon-Lataillade, G., *Effect of an acute exposure of rat testes to gamma rays on germ cells and on Sertoli and Leydig cell functions*, Reprod Nutr Dev 31(6):617-29. (1991) Abstract Only.

Russell, L. D. et al., *Ultrastructural observations of spermatogenesis following transplantation of rat testis cells into mouse seminiferous tubules*, J. Androl 17(6):615-27. (Nov.-Dec. 1996). Abstract Only.

Announcement re Bulsulfan (Myleran) Facts and Comparisons, pp. 1-5 (Aug. 1997).

PCT International Search Report re PCT/US99/10573, International filing Date May 13, 1999, Priority Date: Nov. 13, 1998.

XP-002117132, no date.

PCT, International Search Report re PCT/US99/08277, International Filing date Apr. 15, 1999; Priority Date Nov. 13, 1998.

Derwent, XP-002115938, no date.

Ikawa, Masahito et al., *Green fluorescent protein as a marker in transgenic mice*, Develop. Growth Differ., 37, 455-459 (1995), XP-002086829.

* cited by examiner

GENETIC MODIFICATION OF MALE GERM CELLS FOR GENERATION OF TRANSGENIC SPECIES AND GENETIC THERAPIES

This application is a continuation-in-part of U.S. Ser. No. 09/311,599, filed May 13, 1999, which issued as U.S. Pat. No. 6,734,338 on May 11, 2004, which is a continuation-in-part of U.S. Ser. No. 09/292,723, filed on Apr. 15, 1999, which is a continuation-in-part of U.S. Ser. No. 09/191,920, filed Nov. 13, 1998, which issued as U.S. Pat. No. 6,316,692 B1, on Nov. 13, 2001. This application claims the benefit of U.S. Provisional Application No. 60/065,825, which was filed on Nov. 14, 1997.

The U.S. Government has a paid-up license in this invention and the right in limited circumstances to require the patent owner to license others on reasonable terms as provided for by the terms of NIH Grant No. RO1 RR12406.

BACKGROUND OF THE INVENTION

Throughout this application various publications are referenced within parentheses. The disclosures of these publications in their entireties are hereby incorporated by reference in this application in order to more fully describe the state of the art to which this invention pertains.

1. The Field of the Invention

This invention relates to the medical arts, particularly to the field of transgenics and gene therapy. The invention is particularly directed to in vitro and in vivo methods for genetically modifying male germ cells and support cells (i.e., Leydig and Sertoli cells), which methods incorporate a method of incorporating exogenous genetic material into the genome of a vertebrate to produce transgenic vertebrates and transgenic vertebrate animal lines.

2. Discussion of the Related Art

The field of transgenics was initially developed to understand the action of a single gene in the context of the whole animal and the phenomena of gene activation, expression, and interaction. This technology has been used to produce models for various diseases in humans and other animals. Transgenic technology is amongst the most powerful tools available for the study of genetics, and the understanding of genetic mechanisms and function.

It is also used to study the relationship between genes and diseases. About 5,000 diseases are caused by a single genetic defect. More commonly, other diseases are the result of complex interactions between one or more genes and environmental agents, such as viruses or carcinogens. The understanding of such interactions is of prime importance for the development of therapies, such as gene therapy and drug therapies, and also treatments such as organ transplantation. Such treatments compensate for functional deficiencies and/or may eliminate undesirable functions expressed in an organism.

Transgenesis has also been used for the improvement of livestock, and for the large scale production of biologically active pharmaceuticals. Historically, transgenic animals have been produced almost exclusively by microinjection of the fertilized egg. The pronuclei of fertilized eggs are microinjected in vitro with foreign, i.e., xenogeneic or allogeneic DNA or hybrid DNA molecules. The microinjected fertilized eggs are then transferred to the genital tract of a pseudopregnant female. (E.g., P. J. A. Krimpenfort et al., Transgenic mice depleted in mature T-cells and methods for making transgenic mice, U.S. Pat. Nos. 5,175,384 and 5,434,340; P. J. A. Krimpenfort et al., Transgenic mice depleted in mature lymphocytic cell-type, U.S. Pat. No. 5,591,669).

This widely used technique requires large numbers of fertilized eggs, equipment to handle embryos and the facility to microinject them in vitro. This is partly because there is a high rate of egg loss due to lysis during microinjection. Moreover manipulated embryos are less likely to implant and survive in utero. These factors contribute to the technique's extremely low efficiency. Superovulated mammals (e.g., primates, cows, horses, pigs, and mice) produce only 10-20 or less eggs per female animal per cycle, even after hormonal stimulation, and only 1% of microinjected mouse eggs (Palmiter, R. D. and Brinster, R. L., Germline transformation of mice, Annu. Rev. Genet. 20:465-99 [1986]), and 0.1% of cattle, sheep and pig eggs (Wall, R. J., et al., *Making transgenic livestock: genetic engineering on a large scale*, J. Cell Biochem. 49:113-120 [1992]) develop into transgenic animals. Typically, 300-500 fertilized eggs must be microinjected to produce perhaps three transgenic animals. Consequently, generating large animals with these techniques is prohibitively expensive. For this reason, mammalian transgenic technology has been confined almost exclusively to mice due to their high fecundity. Little has been done to improve the generation of transgenic animals by the microinjection of a transgene into fertilized eggs (Gordon, J. and Ruddle, F. H., *Integration and stable germ line transmission of genes injected into mouse pronuclei*, Science 214:1244-1246 [1981]).

While small animals such as mice have proved to be suitable models for certain diseases, their value in this respect is limited. Larger transgenic animals would be much more suitable than mice for the study of the effects and treatment of most human diseases because of their greater similarity to humans in many aspects, and better for studying organ systems or behavior. Larger mammals are also more suitable than mice as potential organ donors to humans due to the comparable size of their organs. Now that transgenic animals with the potential for human xenotransplantation are being developed, more of these larger animals will be required. Transgenic technology will allow that such donor animals will be immunocompatible with the human recipient.

In contrast to only 10-20 eggs per female even after treatment with superovulatory drugs, most male mammals, including mice and nearly all larger mammals, generally produce at least about $10^8$ spermatozoa (male germ cells) in each ejaculate. For this reason alone, male germ cells will be a better target for introducing foreign DNA into the germ line, leading to the generation of transgenic animals with increased efficiency and after simple, natural mating.

Nevertheless, attempts to generate transgenic mice using spermatozoa to carry DNA into the egg (Lavitrano, M., et al., *Sperm cells as vectors for introduction of DNA into eggs: genetic transformation of mice*, Cell 57: 717-723 [1989]; WO-A-90/08192), have not been validated (Brinster, R. L., et al., *No simple solution for making transgenics*, Cell 59:239-241 [1989]). Recently, transgenic mice were produced after the injection of exogenous DNA together with sperm heads into oocytes (Perry, A. C., et al., *Mammalian transgenesis by intracytoplasmic sperm injection*, Science 284:1180-1183 [1999]). Following uterine transfer, 20% of these embryos developed into transgenic offspring.

Genetic information has been transferred to embryos using retroviral vectors (Jaenisch, R., *Germ line integration and Mendelian transmission of the exogenous Moloney leukemia virus*, Proc. Natl. Acad. Sci. USA 73:1260-1264

[1976]), but the animals were mosaics with different gene insertions in different tissues. (Jaenisch, R., *Retroviruses and embryogenesis: microinjection of Moloney leukemia virus into midgestation mouse embryos*, Cell 19:181-188 [1980]). Recently, five transgenic calves were produced by injection of a pseudotyped replication-deficient vector based on the Moloney murine leukemia virus. The vector was introduced into the perivitelline space of metaphase II oocytes (Chan, A. W., et al., *Transgenic cattle produced by reverse-transcribed gene transfer in oocytes*, Proc. Natl. Acad. Sci. USA 95:14028-14033 [1998]).

An alternative, not yet fully realized, is the stable transfection of male germ cells in vitro and their transfer to a recipient testis. Transfer of genetically marked germ cells to the testis yielded offspring, but so far no transgenic progeny have been produced (Brinster, R. L. and Avarbok, M. R., Germline transmission of donor haplotype following spermatogonial transplantation, Proc. Natl. Acad. Sci. USA 91:11303-11307 [1994]).

Spermatogenesis is the process by which a diploid spermatogonial stem cell provides daughter cells which undergo dramatic and distinct morphological changes to become self-propelling haploid cells (male gametes) capable, when fully mature, of fertilizing an ovum.

Primordial germ cells are first seen in the endodermal yolk sac epithelium at E8 and are thought to arise from the embryonic ectoderm (A. McLaren and M. Buehr, Cell Diff. Dev. 31:185 [1992]; Y. Matsui et al., Nature 353:750 [1991]). They migrate from the yolk sac epithelium through the hindgut endoderm to the genital ridges and proliferate through mitotic division to populate the testis.

At sexual maturity the spermatogonium goes through 5 or 6 mitotic divisions before it enters meiosis. The primitive spermatogonial stem cells (A0/As) proliferate and form a population of intermediate spermatogonia types Apr, Aal, A1-4 after which they differentiate into type B spermatogonia. The type B spermatogonia differentiate to form primary spermatocytes which enter a prolonged meiotic prophase during which homologous chromosomes pair and recombine. The states of meiosis that are morphologically distinguishable are; preleptotene, leptotene, zygotene, and pachytene; secondary spermatocytes and the haploid spermatids are later stages. Spermatids undergo great morphological changes during spermatogenesis, such as reshaping the nucleus, formation of the acrosome and assembly of the tail (A. R. Bellve et al., *Recovery, capacitation, acrosome reaction, and fractionation of sperm*, Methods Enzymol. 225:113-36 [1993]). The spermatocytes and spermatids establish vital contacts with the Sertoli cells through unique hemi-junctional attachments with the Sertoli cell membrane. The final changes in the maturing spermatozoan (i.e., spermatozoon) take place in the genital tract of the female prior to fertilization.

Initially, attempts were made to produce transgenic animals by adding DNA to spermatozoa which were then used to fertilize mouse eggs in vitro. The fertilized eggs were then transferred to pseudopregnant foster females, and of the pups born, 30% were reported to be transgenic and express the transgene. Despite repeated efforts by others, however, this experiment could not be reproduced and no transgenic pups were obtained. Indeed, there remains little doubt that the transgenic animals reputed to have been obtained by this method were not transgenic at all and the DNA incorporation reported was mere experimental artifact. Data collected from laboratories around the world engaged in testing this method showed that no transgenics were obtained from a total of 890 pups generated.

In summary, it is currently possible to produce live transgenic progeny but the available methods are costly and extremely inefficient. Spermatogenic transfection in accordance with this invention, either in vitro or in vivo, provides a simple, less costly and less invasive method of producing transgenic animals and one that is potentially highly effective in transferring allogeneic as well as xenogeneic genes into the animal's germ cells.

To facilitate in vitro transfection of male germ cells and implantation into a testis of a recipient male vertebrate it is advantageous first to depopulate the testis of the recipient vertebrate of untransfected male germ cells before transferring transfected male germ cells into it.

Depopulation of testis has commonly been done by exposing the whole vertebrate to gamma irradiation (X-ray), or localizing irradiation to the testis. (E.g., G. Pinon-Lataillade et al., *Endocrinological and histological changes induced by continuous low dose gamma-irradiation of rat testis*, Acta Endocrinol. (Copenh) 109(4): 558-62 [1985]; G. Pinon-Lataillade and J. Maas, *Continuous gamma-irradiation of rats: dose-rate effect on loss and recovery of spermatogenesis*, Strahlentherapie 161(7):421-26 [1985]; C. R. Hopkinson et al., *The effect of local testicular irradiation on testicular histology and plasma hormone levels in the male rat*, Acta Endocrinol. (Copenh) 87(2):413-23 [1978]; G. Pinon-Lataillade et al., *Influence of germ cells upon Sertoli cells during continuous low-dose rate gamma-irradiation of adult rats*, Mol. Cell. Endocrinol. 58(1):51-63 [1988]; P. Kamtchouing et al., *Effect of continuous low-dose rate gamma-irradiation on rat Sertoli cell function*, Reprod. Nutr. Dev. 28(4B):1009-17 [1988]; C. Pineau et al., *Assessment of testicular function after acute and chronic irradiation: further evidence for influence of late spermatids on Sertoli cell function in the adult rat*, Endocrinol. 124(6): 2720-28 [1989]; M. Kangasniemi et al., *Cellular regulation of basal and FSH-stimulated cyclic AMP production in irradiated rat testes*, Anat. Rec. 227(1):32-36 [1990]; G. Pinon-Lataillade et al., *Effect of an acute exposure of rat testes to gamma rays on germ cells and on Sertoli and Leydig cell functions*, Reprod. Nutr. Dev. 31(6):617-29 [1991]).

The mechanism of gamma radiation-induced spermatogonial degeneration is thought to be related to the process of apoptosis. (M. Hasegawa et al., *Resistance of differentiating spermatogonia to radiation-induced apoptosis and loss in p53-deficient mice*, Radiat. Res. 149:263-70 [1998]).

Another method of depopulating a vertebrate testis is by administering a composition containing an alkylating agent, such as busulfan (Myleran). (E.g., F. X. Jiang, *Behaviour of spermatogonia following recovery from busulfan treatment in the rat*, Anat. Embryol. 198(1):53-61 [1998]; L. D. Russell and R. L. Brinster, *Ultrastructural observations of spermatogenesis following transplantation of rat testis cells into mouse seminiferous tubules*, J. Androl. 17(6):615-27 [1996]; N. Boujrad et al., *Evolution of somatic and germ cell populations after busulfan treatment in utero or neonatal cryptochidism in the rat*, Andrologia 27(4):223-28 [1995]; R. E. Linder et al., *Endpoint of spermatotoxicity in the rat after short duration exposures to fourteen reproductive toxicants*, Reprod. Toxicol. 6(6):491-505 [1992]; F. Kasuga and M. Takahashi, *The endocrine function of rat gonads with reduced number of germ cells following busulfan treatment*, Endocrinol. Jpn 33(1):105-15 [1986]).

Cytotoxic alkylating agents, such as busulfan, chlorambucil, cyclophosphamide, melphalan, or ethyl ethanesulfonic acid, are frequently used to kill malignant cells in cancer chemotherapy. (E.g., Andersson et al., *Parenteral* busulfan for treatment of malignant disease, U.S. Pat. Nos. 5,559,148 and 5,430,057; Stratford et al., Stimulation of stem cell growth by the bryostatins, U.S. Pat. No. 5,358,711; Luck et al., Treatment employing vasoconstrictive substances in combination with cytotoxic agents for introduction into cellular lesion, U.S. Pat. No. 4,978,332). Treatment of mice with busulfan (13 mg-40 mg/kg body wt.), was reported to deplete male germs cells in the testis; both stems cells and differentiating spermatogonia were killed; doses over 30 mg/kg body weight resulted in azoospermia for up to 56 days after treatment. (L. R. Bucci and M. L. Meistrich, *Effects of busulfan on murine spennatogenesis: cytotoxicity, sterility, sperm abnormalities and dominant lethal mutations*, Radiation Research 176:259-68 [1987]).

The present invention addresses the need for spermatogenic genetic modification, either in vitro or in vivo, that is highly effective in transferring allogeneic as well as xenogeneic genes into the animal's germ cells and in producing transgenic vertebrate animals. The present technology addresses the requirements of germ line and stem cell line gene therapies in humans and other vertebrate species, including the need for a superior method of depopulating a testis of untransfected male germ cells. The present technology is of great value in producing transgenic animals in large species as well as for repairing genetic defects that lead to male infertility. Male germ cells that have stably integrated the DNA are selectable. These and other benefits and features of the present invention are described herein.

SUMMARY OF THE INVENTION

The present invention arose from a desire by the present inventors to improve on existing methods for the genetic modification of an animal's germ cells and for producing transgenic animals. The pre-existing art methods rely on direct injection of DNA into zygotes produced in vitro or in vivo, or by the production of chimeric embryos using embryonal stem cells incorporated into a recipient blastocyst. Following this, such treated embryos are transferred to the primed uterus or oviduct. These prior methods are extremely slow and costly, rely on several invasive steps, and only produce transgenic progeny sporadically and unpredictably.

In their search for a less costly, faster, and more efficient approach for producing transgenics, the present inventors devised the present method which relies on the in vivo or in vitro (ex vivo) genetic modification of vertebrate male germ cells with a nucleic acid segment, i.e., a polynucleotide, encoding a desired trait or product.

The present invention relates to the in vivo and in vitro (ex vivo) genetic modification, for example, by transfection or transduction, of vertebrate animal germ cells with a desired genetic material. Briefly, the in vivo method involves injection of genetic material together with a suitable vector directly into the testicle of the animal. In this method, all or some of the male germ cells within the testicle are genetically modified in situ, under effective conditions. The in vitro method involves obtaining germ cells from the gonad (i.e., testis) of a suitable donor or from the animal's own testis, using a novel isolation or selection method, transfecting or otherwise genetically altering them in vitro, and then returning them to the substantially depopulated testis of the donor or of a different recipient male vertebrate under suitable conditions where they will spontaneously repopulate the depopulated testis. The in vitro method has the advantage that the transfected germ cells can be screened by various means before being returned to the testis of the same or a different suitable recipient male to ensure that the transgene is incorporated into the genome in a stable state. Moreover, after screening and cell sorting only enriched populations of germ cells can be returned. This approach provides a greater chance of transgenic progeny after mating.

In particular, the inventive in vivo method of incorporating exogenous genetic material into the genome of a vertebrate involves administering to a male vertebrate's testis(es) a gene delivery mixture comprising a viral vector, such as, but not limited to, a retroviral vector, that comprises at least one polynucleotide defining a gene encoding a desired trait or product and, optionally, a gene encoding a genetic selection marker. The gene(s) are operatively linked to a promoter sequence (all the individual genes used are not necessarily linked to a single promoter sequence), such that a transcriptional unit is formed, and are administered under conditions effective to reach at least one of the spermatozoa, or precursors of spermatozoa, residing in the vertebrate's testis. The delivery mixture, including the polynucleotide(s), are administered in amounts and under conditions effective such that a polynucleotide encoding a desired trait or product is incorporated into the genome of at least one male germ cell, such as a spermatozoan or precursor cell, so that a genetically modified male gamete is produced by the male vertebrate. Then, the male vertebrate is bred, naturally or with the aid of artificial reproductive technologies, with a female vertebrate of its species such that a transgenic progeny is thereby produced that carries the polynucleotide in its genome.

The invention also includes an in vitro method of incorporating at least one polynucleotide encoding a desired trait or product into the genome of a vertebrate. The in vitro method involves obtaining from a donor male vertebrate a male germ cell, such as a spermatozoan cell or a precursor cell, and genetically modifying the cell in vitro with at least one polynucleotide encoding a desired trait or product other than an immortalizing molecule, and a polynucleotide defining a gene encoding a genetic selection marker, in the presence of a gene delivery mixture comprising a viral vector, at about or below the vertebrate's body temperature and for an effective period of time such that the polynucleotide encoding a desired trait or product is incorporated into the genome of the cell. Then the genetically modified germ cell is isolated or selected, with the aid of the genetic selection marker expressed in the genetically modified cell, and transferred to a testis of a recipient male vertebrate such that the cell lodges in a seminiferous tubule of the testis, such that a genetically modified male gamete is produced therein. The male vertebrate is bred with a female vertebrate of its species such that a transgenic progeny is thereby produced that carries the polynucleotide in its genome.

This invention also relates to a non-human transgenic male vertebrate produced in accordance with either the in vivo or in vitro method of incorporating exogenous genetic material into the genome of a vertebrate. Produced in accordance with the in vivo method, the transgenic vertebrate is the recipient of the gene delivery mixture. Produced in accordance with the in vitro method, the transgenic vertebrate is the recipient of the genetically modified male germ cell that was transferred to its testis. The transgenic male vertebrate can be bred with a female of its species, because it comprises a native male germ cell carrying in its genome a polynucleotide of exogenous origin defining a gene encoding a desired trait or product. But somatic cells in tissues outside the testis of the transgenic vertebrate lack the polynucleotide.

This invention also relates to a non-human transgenic vertebrate produced in accordance with either the in vivo or in vitro method of incorporating exogenous genetic material into the genome of a vertebrate. The non-human transgenic vertebrate is the direct or indirect progeny of the male vertebrate that received the gene delivery mixture, in accordance with the in vivo method. Alternatively, the non-human transgenic vertebrate is the direct or indirect progeny of the recipient of the genetically modified male germ cell that was transferred to its testis, in accordance with the in vitro method. Thus, the transgenic progeny is the immediate offspring of the transgenic male vertebrate, or is an offspring thereof separated by one or more generations. The transgenic vertebrate includes one or more cells carrying in their genome a polynucleotide of exogenous origin that encodes a desired trait or product.

Also, the invention includes a transgenic cell derived from the transgenic progeny. The cell is a germ cell, such as a spermatozoan (i.e., spermatozoon) or ovum, a precursor cell of either of these, or a somatic cell.

The invention also relates to vertebrate semen containing a plurality of the inventive transgenic male germ cell.

The invention is also directed to a method of producing a non-human transgenic vertebrate animal line comprising native germ cells carrying in their genome at least one xenogeneic polynucleotide. The method involves breeding of the transgenic progeny with a member of the opposite sex of the same species; and selecting its progeny for the presence of the polynucleotide.

This technology is applicable to the production of transgenic animals for use as animal models, and to the modification of the genome of an animal, including a human, by addition, modification, or subtraction of genetic material, often resulting in phenotypic changes. The present methods are also applicable to altering the carrier status of an animal, including a human, where that individual is carrying a gene for a recessive or dominant gene disorder, or where the individual is prone to pass a multigenic disorder to his offspring.

These and other advantages and features of the present invention will be described more fully in a detailed description of the preferred embodiments which follows. In further describing the invention, the disclosures of related applications U.S. Ser. Nos. 09/191,920; 09/292,723; and 09/311,599 are incorporated by reference.

BRIEF DESCRIPTION OF THE DRAWINGS

FIG. 1 illustrates the process of microinjection of gene delivery mixture into a mammalian (mouse) testis.

FIG. 2 shows testicular cells transduced by a pseudotyped lentiviral vector expressing Green Fluorescent Protein (GFP) in Zeiss 410 confocal images (wavelength 488 nm; 19 stacked images) of a cryosection of mouse testis.

DETAILED DESCRIPTION OF THE PREFERRED EMBODIMENTS

Figure 1A:
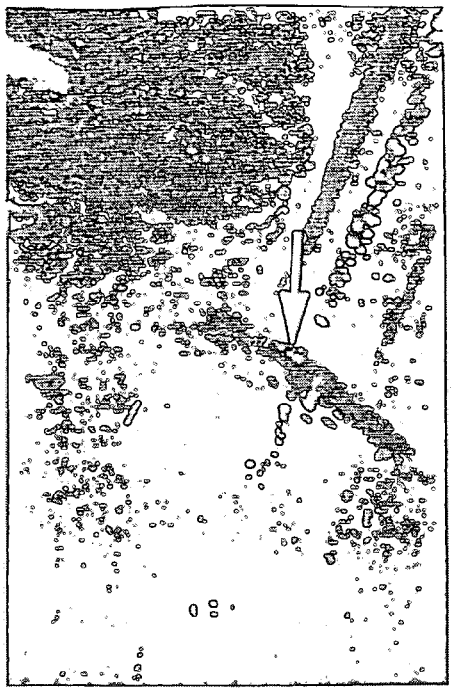
FIG. 1(a) shows a preferred site of microinjection into a vas efferens; in mammals, the vasa efferentia connect to the lumen of all seminiferous tubules.

The present method of incorporating exogenous genetic material into the genome of a vertebrate relies on at least one of the following strategies. A first method, an in vivo method of incorporating exogenous genetic material into the genome of a vertebrate, delivers a polynucleotide using known gene delivery systems to male germ cells in situ in the testis of the male vertebrate (e.g., in vivo transfection or transduction), allows the genetically modified germ cells to differentiate in their own milieu, and then selects for progeny animals exhibiting the nucleic acid's integration into its germ cells (transgenic animals). The thus selected progeny can be mated, or their sperm utilized for insemination or in vitro fertilization to produce further generations of transgenic progeny.

Alternatively, the in vitro method of incorporating exogenous genetic material into the genome of a vertebrate involves obtaining male germ cells from the testis of a suitable donor or from the animal's own testis, genetically modifying them in vitro, isolating or selecting genetically modified germ cells, and then transferring them to the testis under suitable conditions where they will spontaneously repopulate it.

By either the in vivo or in vitro route, the inventive method is suitable for application to a variety of vertebrate animals, all of which are capable of producing gametes, i.e. sperm or ova. Thus, in accordance with the invention novel genetic modification(s) and/or characteristic(s) can be imparted to vertebrates, including mammals, such as humans, non-human primates, for example simians, marmosets, domestic agricultural animals such as ovines (e.g., sheep), bovines (e.g., cattle), porcines (e.g., pigs), equines (e.g., horses), particularly race horses, marine mammals, feral animals, rodents such as mice and rats, gerbils, hamsters, rabbits, and the like. Other vertebrate animals include fowl such as chickens, turkeys, ducks, ostriches, emus, geese, guinea fowl, doves, quail, rare and ornamental birds, and the like. Of particular interest are endangered species of wild animal, such as rhinoceros, tigers, cheetahs, species of condor, and the like.

"Gene delivery (or transfection) mixture", in the context of this patent, means selected genetic material together with an appropriate vector mixed, for example, with an effective amount of lipid transfecting agent, for example, a cationic or polycationic lipid, such as polybrene. (E.g., Clark et al., *Polycations and cationic lipids enhance adenovirus transduction and transgene expression in tumor cells*, Cancer Gene Ther. 6(5):437-46 [1999]). The efficiency of adenoviral-, retroviral-, or lentiviral-mediated transduction is enhanced significantly by including polybrene during the infection. The amount of each component of the mixture is chosen so that the genetic modification, e.g., by transfection or transduction, of a specific species of male germ cell is optimized. Such optimization requires no more than routine experimentation. The ratio of DNA to lipid is broad, preferably about 1:1, although other proportions can also be utilized depending on the type of lipid transfecting agent used. (E.g., Banerjee, R. et al. [1999]; Jaaskelainen, I. et al., *A lipid carrier with a membrane active component and a small complex size are required for efficient cellular delivery of anti-sense phosphorothioate oligonucleotides*, Eur. J. Pharm. Sci. 10(3):187-193 [2000]; Sakurai, F. et al., *Effect of DNA/liposome mixing ratio on the physicochemical characteristics, cellular uptake and intracellular trafficking of plasmid DNA/cationic liposome complexes and subsequent gene expression*, J. Controlled Release 66(2-3):255-69 [2000]).

"Genetic material", as used herein, means DNA sequences capable of imparting novel genetic modification(s), or biologically functional characteristic(s), to the recipient animal. The novel genetic modification(s) or characteristic(s) can be encoded by one or more genes or gene segments defined by a polynucleotide, or can be caused by removal or mutation of one or more genes, and can additionally contain regulatory sequences, such as, but not limited to enhancers, promoters, or activator/suppressor binding sites. The transfected genetic material is preferably functional, that is it expresses a desired trait by means of a product or by suppressing the production of another. Examples of other mechanisms by which a gene's function can be expressed are genomic imprinting, i.e. inactivation of one of a pair of genes (alleles) during very early embryonic development, or inactivation of genetic material by mutation or deletion of gene sequences, or by repression of a dominant negative gene product, among others.

The desired product is any preselected product other than an immortalizing molecule, such as SV40 large T or polyoma virus large T antigens. An immortalizing molecule can transform cells into "cancer-like" cells. "Immortalization" resulting from the expression of an immortalizing molecule can cause a male germ cell to lose many of its important germ cell characteristics, for instance the ability to undergo meiosis, which is crucial for the production of normally functioning male gametes. (E.g., see, Wolkowicz, M. J., Coonrod, S. M., Reddi, P. P. Millan, J. L., Hofmann, M-C, Herr, J. C., *Refinement of the differentiated phenotype of the spermatogenic cell line GC-2spd(ts)*, Biology of Reproduction 55:923-32 [1996]). Male germ cells genetically modified to express an immortalizing molecule are, therefore, not useful for the production of transgenic vertebrate progeny in accordance with the present invention.

In addition, novel genetic modification(s) can be artificially induced mutations or variations, or natural allelic mutations or variations of a gene(s). Mutations or variations can be induced artificially by a number of techniques, all of which are well known in the art, including chemical treatment, gamma irradiation treatment, ultraviolet radiation treatment, ultraviolet radiation, the use of specific chimeric DNA/RNA oligonucleotides (chimeraplasty), and the like. Chemicals useful for the induction of mutations or variations include carcinogens such as ethidium bromide and others known in the art.

DNA segments of specific sequences can also be constructed to thereby incorporate any desired mutation or variant or to disrupt a gene or to alter genomic DNA. Those skilled in the art will readily appreciate that the genetic material is inheritable and is, therefore, present in almost every cell of future generations of the progeny, including the germ cells. Among novel characteristics are the expression of a previously unexpressed trait, augmentation or reduction of an expressed trait, over expression or under expression of a trait, ectopic expression, that is expression of a trait in tissues where it normally would not be expressed, or the attenuation or elimination of a previously expressed trait. Other novel characteristics include the qualitative change of an expressed trait, for example, to palliate or alleviate, or otherwise prevent expression of an inheritable disorder with a multigenic basis.

"Transfecting agent", as utilized herein, means a composition of matter added to the genetic material for enhancing the uptake of exogenous DNA segment(s) into a eukaryotic cell, preferably a mammalian cell, and more preferably a mammalian germ cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. These complexes can be targeted to the male germ cells using specific ligands which are recognized by receptors on the cell surface of the germ cell, such as the c-kit ligand or modifications thereof.

Other preferred transfecting agents include lipofectin, lipfectamine, DIMRIE C, Superfect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, or poly(ethylenimine) (PEI). (E.g., Banerjee, R. et al., *Novel series of non-glycerol-based cationic transfection lipids for use in liposomal gene delivery*, J. Med. Chem. 42(21):4292-99 [1999]; Godbey, W. T. et al., *Improved packing of poly(ethylenimine/DNA complexes increases transfection efficiency*, Gene Ther. 6(8): 1380-88 [1999]; Kichler, A et al., *Influence of the DNA complexation medium on the transfection efficiency of lipospermine/DNA particles*, Gene Ther. 5(6):855-60 [1998]; Birchaa, J. C. et al., *Physico-chemical characterisation and transfection efficiency of lipid-based gene delivery complexes*, Int. J. Pharm. 183(2): 195-207 [1999]). These non-viral agents have the advantage that they facilitate stable integration of xenogeneic DNA sequences into the vertebrate genome, without size restrictions commonly associated with virus-derived transfecting agents.

"Virus", as used herein, means any virus, or transfecting fragment thereof, which can facilitate the delivery of the genetic material into male germ cells. Examples of the pipette can be introduced into the rete testis or the tubule system of the testicle, with the aid of a binocular microscope with coaxial illumination, with care taken not to damage the wall of the tubule opposite the injection point, and keeping trauma to a minimum. On average, a magnification of about 25× to 80× is suitable, and bench mounted micromanipulators are not severally required as the procedure can be carried out by a skilled artisan without additional aids. A small amount of a suitable, non-toxic dye, can be added to the gene delivery mixture (fluid) to confirm delivery and dissemination to the seminiferous tubules of the testis. It can include a dilute solution of a suitable, non-toxic dye, which can be visualized and tracked under the microscope.

In this manner, the gene delivery mixture reaches and is brought into intimate contact with the male germ cells. Male germ cells include spermatozoa (i.e., male gametes) and developmental precursors thereof. In fetal development, primordial germ cells are thought to arise from the embryonic ectoderm, and are first seen in the epithelium of the endodermal yolk sac at the E8 stage. From there they migrate through the hindgut endoderm to the genital ridges. In the sexually mature male vertebrate animal, there are several types of cells that are precursors of spermatozoa, and which can be genetically modified, including the primitive spermatogonial stem cells, known as A0/As, which differentiate into type B spermatogonia. The latter further differentiate to form primary spermatocytes, and enter a prolonged meiotic prophase during which homologous chromosomes pair and recombine. Useful precursor cells at several morphological/developmental stages are also distinguishable: preleptotene spermatocytes, leptotene spermatocytes, zygotene spermatocytes, pachytene spermatocytes, secondary spermatocytes, and the haploid spermatids. The latter undergo further morphological changes during spermatogenesis, including the reshaping of their nucleus, the formation of acrosome, and assembly of the tail. The final changes in the spermatozoan (i.e., male gamete) take place in the genital tract of the female, prior to fertilization. The polynucleotide contained in the gene delivery mixture administered in the in vivo method to the testis will reach germ cells that are at any one of the above described stages, and will be taken up preferentially by those that are at a relatively more receptive stage.

In the in vitro (ex vivo) method of incorporating exogenous genetic material into the genome of a vertebrate, the male germ cells are preferably, but not exclusively, viruses which are suitable for use herein are adenoviruses, adeno-associated viruses, retroviruses such as human immunedeficiency virus, lentiviruses, mumps virus, and transfecting fragments of any of these viruses, and other viral DNA segments that facilitate the uptake of the desired DNA segment by, and release into, the cytoplasm of germ cells and mixtures thereof. A preferred viral vector is Moloney murine leukemia virus and the retrovirus vector derived from Moloney virus called vesicular-stomatitis-virus-glycoprotein (VSV-G)-Moloney murine leukemia virus. A most preferred viral vector is a pseudotyped (VSV-G) lentiviral vector derived from the HIV virus (Naldini et al. [1996]). Also, the mumps virus is particularly suited because of its affinity for immature sperm cells including spermatogonia. All of the above viruses may require modification to render them non-pathogenic or less antigenic. Other known vector systems, however, are also useful within the confines of the invention.

In the in vivo method of incorporating exogenous genetic material into the genome of a vertebrate, administering to a male vertebrate's testis a gene delivery mixture involves the in vivo introduction of the gene delivery mixture to the germ cells by direct delivery into at least one of the animal's testes, where it is distributed to male germ cells at various stages of development. The in vivo method employs injection of the gene delivery mixture, preferably into the seminiferous tubules, or into the rete testis, and most preferably into the vas efferens or vasa efferentia, using, for example, a micropipette. To ensure a steady infusion of the gene delivery mixture, under pressures which will not damage the delicate tubule system in the testis, the injection is made through the micropipette with the aid of a picopump delivering a precise measured volume under controlled amounts of pressure. The micropipette is made of a suitable material, such as, metal or glass, and is usually made from glass tubing which has been drawn to a fine bore at its working tip, e.g. using a pipette puller. The tip can be angulated in a convenient manner to facilitate its entry into the testicular tubule system. Also, the micropipette can be provided with a beveled working end to allow a better and less damaging penetration of the fine tubules at the injection site. This bevel can be produced by means of a specially manufactured grinding apparatus. The diameter of the tip of the pipette for the in vivo method of injection is typically about 15 to 45 microns, although other sizes can be used as needed, depending on the animal's size. The tip of diploid spermatogonia, which are exposed to or contacted with the gene delivery mixture.

Whether employed in the in vivo method or in vitro method, the gene delivery mixture, once in contact with the male germ cells, facilitates the uptake and transport of exogenous genetic material into the appropriate cell location for integration into the genome and expression. A number of known gene delivery methods can be used for the uptake of nucleic acid sequences into the cell. In either the in vivo or vitro method, the gene delivery mixture typically comprises the polynucleotide encoding the desired trait or product, together with a suitable promoter sequence, and optionally agents which increase the uptake of or comprise the polynucleotide sequence, such as liposomes, retroviral vectors, adenoviral vectors, adenovirus enhanced gene delivery systems, or combinations thereof. A reporter construct, including a genetic selection marker, such as the gene encoding for Green Fluorescent Protein, can further be added to the gene delivery mixture. Targeting molecules, such as c-kit ligand, can be added to the gene delivery mixture to enhance the transfer of genetic material into the male germ cell. An immunosuppressing agent, such as cyclosporin or a corticosteroid can also be added to the gene delivery mixture as known in the art.

In the in vitro method of incorporating exogenous genetic material into the genome of a vertebrate, the male germ cells are obtained or collected from the donor male vertebrate, by means known in the art. The thus obtained germ cells are then exposed to the gene delivery mixture, preferably within several hours, or cryopreserved for later use.

In one embodiment of the in vitro method, obtaining the male germ cells from the donor vertebrate can be accomplished by transection of the testes. Transection of the isolated testicular tissue can be accomplished, for example, by isolation of the vertebrate's testes, decapsulation and teasing apart and mincing of the seminiferous tubules. The separated cells can then be incubated in an enzyme mixture comprising enzymes known for gently breaking up the tissue matrix and releasing undamaged cells such as, for example, pancreatic trypsin, collagenase type I, pancreatic DNAse type I, as well as bovine serum albumin and a modified DMEM medium. The cells can be incubated in the enzyme mixture for a period of about 5 min to about 30 min, more preferably about 15 to about 20 min, at a temperature of about 33° C. to about 37° C., more preferably about 36 to 37° C. After washing the cells free of the enzyme mixture, they can be placed in an incubation medium such as DMEM, and the like, and plated on a culture dish for genetic modification by exposure to the gene delivery mixture. This transection method is not suitable when the donor and recipient male vertebrates are intended to be the same animal, in which case induced a less destructive biopsy method or induced ejaculation by means known in the art is preferred.

Any of a number of commercially available gene delivery mixtures can be used, to which the polynucleotide encoding a desire trait or product is further admixed. The final gene delivery mixture comprising the polynucleotide can then be admixed with the cells and allowed to interact for a period of about 2 hrs to about 16 hrs, preferably about 3 to 4 hrs, at a temperature of about 33° C. to about 37° C., preferably about 36° C. to 37° C., and more preferably in a constant and/or controlled atmosphere. After this period, the cells are preferably placed at a lower temperature of about 33° C. to about 34° C., preferably about 30-35° C. for a period of about 4 hrs to about 20 hrs, preferably about 16 to 18 hrs. Other conditions which do not deviate radically from the ones described can also be utilized as an artisan would know.

With respect to either the in vivo or in vitro methods, a most preferred embodiment employs a retroviral vector system, which was developed for gene therapy (Naldini, L., et al., *In vivo gene delivery and stable transduction of nondividing cells by a lentiviral vector*, Science 272: 263-267 [1996]), which is used to transduce male germ cells in vivo or in vitro. This gene delivery system employs retroviral particles generated by a three-plasmid expression system. In this system a packaging construct contains the human cytomegalovirus (hCMV) immediate early promoter, driving the expression of all viral proteins. The construct's design eliminates the cis-acting sequences crucial for viral packaging, reverse transcription and integration of these transcripts. The second plasmid encodes a heterologous envelope protein (env), namely the G glycoprotein of the vesicular stomatitis virus (VSV-G). The third plasmid, the transducing vector (pHR'), contains cis-acting sequences of human immunodeficiency virus (HIV) required for packaging, reverse transcription and integration, as well as unique restriction sites for cloning heterologous complementary DNAs (cDNAs). For example, a genetic selection marker, such as the enhanced green fluorescent protein (EGFP), and/or a gene encoding another preselected or desired trait or product is cloned downstream of the hCMV promoter in the HR' vector, and is operatively linked so as to form a transcriptional unit. A VSV-G pseudotyped retroviral vector system is capable of infecting a wide variety of cells including cells from different species and of integrating into the genome. Some retroviruses, i.e., lentiviruses, such as HIV, have the ability to infect non-dividing cells. They have a limited capacity for heterologous DNA sequences, the size limit for this vector being 7-7.5 kilobases (Verma, I. M. and Somia, N., *Gene Therapy—promises, problems and prospects*, Nature 389:239-242 [1997]). In vivo experiments with lentiviruses show that expression does not shut off like other retroviral vectors and that in vivo expression in brain, muscle, liver or pancreatic-islet cells, is sustained at least for over six months—the longest time tested so far (Verma and Somia [1997]; Anderson, W F., *Human Gene Therapy*, Nature (Suppl). 392:25-30 [1998]).

For the expression of delivered genetic material by transfection, transduction, or other means to obtain expression of a desired trait or product, a promoter sequence is operatively linked to a polynucleotide sequence encoding the desired trait or product. For purposes of the present invention, "operatively linked" means that, within a transcriptional unit, the promoter sequence, is located upstream (i.e., 5' in relation thereto) from the coding sequence and the coding sequence, is 3' to the promoter, or alternatively is in a sequence of genes 3' to the promoter and expression is coordinately regulated thereby. Both the promoter and coding sequences are oriented in a 5' to 3' manner, such that transcription can take place in vitro in the presence of all essential enzymes, transcription factors, co-factors, activators, and reactants, under favorable physical conditions, e.g., suitable pH and temperature. This does not mean that, in any particular cell, conditions will favor transcription. For example, transcription from a tissue-specific promoter is generally not favored in heterologous cell types from different tissues.

A promoter sequence is chosen that operates in the cell type of interest and/or under the physiologic or developmental conditions of interest. Useful promoter sequences include constitutive promoters, such as, but not limited to, cytomegalovirus (CMV) promoter, or inducible promoters, such as, but not limited to, the human C-reactive protein (CRP) promoter (e.g., Kanzler, S., et al., *TGF-beta1 in liver fibrosis: an inducible transgenic mouse model to study liver fibrogenesis*, Am. J. Physiol. 276(4Pt 1):G1059-68 [1999]), or the insulin-like growth factor (IGF-I) promoter (e.g., Meton I., et al., *Growth hormone induces insulin-like growth factor-I gene transcription by synergistic action of STAT5 and HNF-1alpha*, FEBS Lett. 444(2-3):155-59 [1999]). Useful promoters include those that promote transcription in cells of diverse tissues, such as, but not limited to, an insulin receptor (IR) gene promoter (e.g., Tewari, D. S., et al., *Characterization of the promoter region and 3' end of the human insulin receptor gene*, J. Biol. Chem. 264(27):16238-45 [1989]); growth hormone receptor (GHR)P2 or P3 promoters (e.g., Jiang, H., et al., *Isolation and characterization of a novel promoter for the bovine growth hormone receptor gene*, J. Biol. Chem. 274(12):7893-900 [1999]); or a leptin promoter (e.g., Chen, X. L., et al., *Analysis of a 762-bp proximal leptin promoter to drive and control regulation of transgene expression of growth hormone receptor in mice*, Biochem. Biophys. Res. Commun. 262(1):187-92 [1999]).

Also useful for various applications are tissue-selective (i.e., tissue-specific) promoters, i.e., promoters from which expression occurs preferentially in cells of a particular kind of tissue, compared to one or more other types of tissue. Tissue-specific promoters are particularly useful in applications directed to gene therapy or to the genetic enhancement of non-human vertebrates.

For example, a promoter sequence, which is only active in cycling spermatogonial stem cell populations can be used for differential expression in male germ cells, for example, B-Myb or a male germ cell-specific promoter, such as the c-kit promoter region, c-raf-1 promoter, ATM (ataxia-telangiectasia) promoter (also active in cerebellar cells and thymocytes), vasa promoter, cyclin A1promoter, RBM (ribosome binding motif) promoter, DAZ (deleted in azoospermia) promoter, XRCC-1 promoter, HSP 90 (heat shock gene) promoter, or FRMI (from fragile X site) promoter.

For hematopoietic tissue-selective expression in hematopoietic precursor cells, useful promoters include cyclin A1 promoters (e.g., Müller, C., et al., *Cloning of the cyclin A1 genomic structure and characterization of the promoter region*, J. Biol. Chem. 276(16): 11220-28 [1999]); CD34 promoters (e.g., Burn, T. C., et al., Hematopoietic stem cell specific gene expression, U.S. Pat. No. 5,556,954); a c-kit promoter, or an integrin alphaIIb promoter (e.g., Wilcox, D. A., et al., *Integrin alphaIIb promoter-targeted expression of gene products in megakaryocytes derived from retrovirus-transduced human hematopoietic cells*, Proc. Natl. Acad. Sci. USA 96(17):9654-59 [1999]).

Cartilage-selective promoters for expression in chondrocytes, for example, an osteocalcin (OC) promoter (e.g., Newberry, E. P., et al., *The RRM domain of MINT, a novel Msx2 binding protein, recognizes and regulates the rat osteocalcin promoter*, Biochemistry 38(33):10678-90 [1999]); a SOX9 promoter, aggrecan gene promoter (AGC1), or collagen oligomeric matrix protein (COMP) gene promoter (e.g., Kanai, Y. & Koopman, P., *Structural and functional characterization of the mouse Sox9 promoter: implications for campomelic dysplasia*, Hum. Mol. Genet. 8(4):691-96 [1999]; Newton et al., *Characterization* of human and mouse cartilage oligomeric matrix protein, Genomics 24:435-39 [1994]; or a promoter from a collagen gene, such as, but not limited to promoters for COL2A1, COL9A1, or COL10A1. (e.g., Ganguly, A., et al., *Targeted insertions of two exogenous collagen genes into both alleles of their endogenous loci in cultured human cells: the insertions are directed by relatively short fragments containing the promoters and the 5' ends of the genes*, Proc Natl Acad Sci USA 91(15):7365-9 [1994]; Dharmavaram, R. M., et al., *Detection and characterization of Sp1 binding activity in human chondrocytes and its alterations during chondrocyte dedifferentiation*, J. Biol Chem 272(43):26918-25 [1997]; Zhou, G., et al., *Three high mobility group-like sequences within a 48-base pair enhancer of the Col2a1 gene are required for cartilage-specific expression in vivo*, J. Biol Chem 273(24):14989-97 [1998]; Seghatoleslami, M. R., et al., *Differential regulation of COL2A1 expression in developing and mature chondrocytes*, Matrix Biol 14(9):753-64 [1995]; Lefebvre, V., et al., *An 18-base-pair sequence in the mouse proalpha1(II) collagen gene is sufficient for expression in cartilage and binds nuclear proteins that are selectively expressed in chondrocytes*, Mol Cell Biol 16(8):4512-23 [1996]; Zhou, G., et al., *A 182 bp fragment of the mouse pro alpha 1(II) collagen gene is sufficient to direct chondrocyte expression in transgenic mice*, J. Cell Sci, 108(Pt 12):3677-84 [3677-84]; Mukhopadhyay, K., et al., *Use of a new rat chondrosarcoma cell line to delineate a 119-base pair chondrocyte-specific enhancer element and to define active promoter segments in the mouse pro-alpha 1(II) collagen gene*, J. Biol Chem 270(46):27711-9 [1995]; Vikkula, M., et al., *Structural analysis of the regulatory elements of the tyupe-II procollagen gene. Conservation of promoter and first intron sequences between human and mouse*, Biochem J 285(Pt 1):287-94 [1992]; Beier, F., et al., *Localization of silencer and enhancer elements in the human type X collagen gene*, J Cell Biochem 662(2):210-8 [1997]; Thomas, J. T., *Sequence comparison of three mammalian type-X collagen promoters and preliminary functional analysis of the human promoter*, Gene 160(2):291-6 [1995]; Apte, S. S., *Characterization of the mouse type X collagen gene*, Matrix 13(2): 165-79 [1993]). A cartilage-derived retinoic acid-sensitive protein (CD-RAP) gene promoter is also useful for cartilage-selective expression by chondrocytes. (e.g., Xie, W. F., et al., *Transactivation of the mouse cartilage derived retinoic acid-sensitive protein gene by Sox9*, J. Bone Miner. Res. 14(5):757-63 [1999]).

For liver-selective expression in hepatocytes, useful promoter sequences include, an albumin gene promoter (e.g., Pastore, L., et al., *Use of a liver-specific promoter reduces immune response to the transgene in adenoviral vectors*, Hum. Gen. Ther. 10(11): 1773-81 [1999]); a CYP7A or CYP7A1 promoter (e.g., Nitta, M., et al., *CPF: an orphan nuclear receptor that regulates liver-specific expression of the human cholesterol 7alpha-hydroxylase gene*, Proc. Natl. Acad. Sci. USA 96(12):6660-65 [1999]; Chen, J., et al., *Hepatocyte nuclearfactor 1 binds to and transactivates the human but not the rat CYP7A1 promoter*, Biochem. Biophys. Res. Commun. 260(3):829-34 [1999]); a GHR P1 promoter (e.g., Zou, L., et al., *Isolation of a liver-specific promoter for human growth hormone receptor gene*, Endocrinology 138(4):1771-74 [1997]; Jiang, H., et al. [1999]; Adams, T. E., *Differential expression of growth hormone receptor messenger RNA from a second promoter*, Mol. Cell. Endocrinol. 108(1-2):23-33 [1995]); or a thrombin-activatable fibrinolysis inhibitor (TAFI) promoter (e.g., Boffa, M. B., et al., *Characterization of the gene encoding human TAFI [thrombin-activatable fibrinolysis inhibitor; plasma procarboxypeptidase B]*, Biochemistry 38(20):6547-58 [1999]).

Neuronal specific promoters are also useful, for example, a neurofilament promoter or a neural-specific enolase promoter.

Many other tissue specific promoters are useful for tissue specific expression of a preselected gene for phenotypic expression of a desired trait or product in the various tissues or organs of the vertebrate body.

Other useful promoters are related to the expression of cytokine-inducible proteins, including promoters that regulate the expression of products and modulators of the Jak-STAT signaling cascade, for example, a SOCS-3 promoter (C. J. Auemhammer et al., *Autoregulation of pituitary corticotroph SOCS-3 expression: characterization of the murine SOCS-3 promoter*, Proc. Natl. Acad. Sci. USA 96:6964-69 [1999]), a STAT-3 promoter (C. Bousquet & S. Melmed, J. Biol. Chem. 274:10723-30 [1999]), a POMC promoter (C. J. Auemhammer et al. [1998b]), or Spi 2.1 promoter (T. E. Adams et al. [1995]).

Useful promoters also include exogenously inducible promoters. These are promoters that can be "turned on" in response to an exogenously supplied agent or stimulus, which is generally not an endogenous metabolite or cytokine. Examples include an antibiotic-inducible promoter, such as a tetracycline-inducible promoter; a heat-inducible promoter; a light-inducible promoter; or a laser-inducible promoter. (E.g., Halloran, M. C. et al., *Laser-induced gene expression in specific cells of transgenic zebrafish*, Development. 127(9):1953-1960 [2000]; Gerner, E. W. et al., *Heat-inducible vectors for use in gene therapy*, Int. J. Hyperthermia 16(2):171-81 [2000]; Rang, A. and Will, H., *The tetracycline-responsive promoter contains functional interferon-inducible response elements*, Nucleic Acids Res. 28(5):1120-5 [2000]; Hagihara Y. et al., *Long-term functional assessment of encapsulated cells transfected with Tet-On system*, Cell Transplant. 8(4):431-4 [1999]; Huang, C. J. et al., *Expression of green fluorescent protein in oligodendrocytes in a time-and level-controllable fashion with a tetracycline-regulated system*, Mol. Med. 5(2):129-37 [1999]; Forster, K. et al., *Tetracycline-inducible expression systems with reduced basal activity in mammalian cells*, Nucleic Acids Res. 27(2):708-10 [1999]; Liu, H. S. et al., *Lac/Tet dual-inducible system functions in mammalian cell lines*, Biotechniques 24(4):624-8, 630-2 [1998]).

Other useful promoters include developmentally or temporally regulated promoters. Examples include the myelin P0 promoter (P. Thatikunta et al., *Reciprocal Id expression and myelin gene regulation in Schwann cells*, Mol. Cell. Neurosci. 14(6):519-28 [1999]), Gabra3 or GABRA3 promoters (W. Mu and D. R. Burt, *the mouse GABA(A) receptor alpha3 subunit gene and promoter*, Brain Res. Mol. Brain. Res. 73(1-2): 172-80 [1999]), tyrosine hydroxylase promoter (J. J. Schimmel et al., *4.5 kb of the rat tyrosine hydroxylase 5' flanking sequence directs tissue specific expression during development and contains consensus sites for multiple transcription factors*, Brain Res. Mol. Brain. Res. 74(1-2): 1-14 [1999]), vimentin promoters (A. Benazzouz and P. Duprey, *The vimentin promoter as a tool to analyze the early events of retinoic acid-induced differentiation of cultured embryonal carcinoma cells*, Differentiation (65(3):171-80 [1999]), GATA-6 promoters (A. Brewer et al., *The human and mouse GATA-6 genes utilize two promoters and two initiation codons*, J. Biol. Chem. 274 (53):38004-16 [2000]), SHIP1 or SHIP2 promoters (S. Schurmans et al., *The mouse SHIP2 (Inppl1)gene: comple-* mentary DNA, genomic structure, promoter analysis, and gene expression in the embryo and adult mouse, Genomics 62(2):260-71 [1999]), or hGH-N promoters (B. M. Shewchuk et al., *Pit-1 binding sites at the somatotrope-specific DNase I hypersensitive sites I, II, of the human growth hormone locus control region are essentialfor in vivo hGH-N gene activation*, J. Biol. Chem. 274(50):35725-33 [1999]).

The foregoing examples of useful promoter sequences are by no means an exhaustive list, but are merely illustrative of the promoters available to the skilled artisan in practicing the present invention.

The in vivo and in vitro methods of incorporating exogenous genetic material into the genome of a vertebrate involve incorporating the polynucleotide encoding a desired trait or product into the genome of at least one spermatozoan or precursor thereof, so that a genetically modified male gamete is produced by the male vertebrate. Thus, the genetically modified germ cells of the vertebrate animal, now transgenic, have the non-endogenous (exogenous) genetic material integrated into their chromosomes. This is what is often referred to as a "stable transfection" or "stable integration". This is applicable to all vertebrate animals, including humans. Animals that are shown to carry suitably modified sperm cells then can be either allowed to mate naturally, or alternatively their spermatozoa are used for insemination or in vitro fertilization.

Isolating and/or selecting of genetically modified cells, including transgenic germ cells and transgenic somatic cells, and of transgenic vertebrates, is by any suitable means, such as, but not limited to, physiological and/or morphological phenotypes of interest using any suitable means, such as biochemical, enzymatic, immunochemical, histologic, electrophysiologic, biometric or like methods; and analysis of cellular nucleic acids, for example the presence or absence of specific DNAs or RNAs of interest using conventional molecular biological techniques, including hybridization analysis, nucleic acid amplification (such as but not limited to, polymerase chain reaction [PCR], reverse transcriptase-mediated polymerase chain reaction [RT-PCR], transcription-mediated amplification [TMA], reverse transcriptase-mediated ligase chain reaction [RT-LCR]), and/or electrophoretic technologies.

In a preferred embodiment, the gene delivery mixture includes at least one polynucleotide comprising a gene encoding a genetic selection marker that is operatively linked to a promoter sequence such that a transcriptional unit is formed. The promoter sequence can be the same or different from the promoter regulating the expression from the gene encoding the desired trait or product. The genetic selection marker, also known as a reporter gene, is, for example, a gene encoding an enzyme, such as β-galactosidase, or encoding a fluorescent protein, such as Green Fluorescent Protein (GFP), enhanced Green Fluorescent Protein (EGFP), Yellow Fluorescent Protein, Blue Fluorescent Protein, a phycobiliprotein, such as phycoerythrin or phycocyanin, or any other protein which fluoresces under a suitable wave-length.

Another preferred genetic selection marker or reporter gene, suitable for some applications is a gene encoding a protein that can enzymatically lead to the emission of light from a substrate(s); for purposes of the present invention, such a protein is a "light-emitting" or luminescent protein. For example, a light-emitting protein includes proteins such as luciferase or apoaequorin. Transgenic cells expressing a fluorescent or luminescent protein encoded by the reporter construct can be sorted with the aid of, for example, a flow activated cell sorter (FACS) set at the appropriate wavelength(s), or they can be selected by chemical methods.

A preferred method of isolating or selecting male germ cell populations, comprises obtaining specific male germ cell populations, such as spermatogonia, from a mixed population of testicular cells by extruding the cells from the seminiferous tubules and gentle enzymatic disaggregation. The spermatogonia or other male germ cell populations, which are to be genetically modified, can be isolated from a mixed cell population by a method including the utilization of a promoter sequence, which is specifically or selectively active in cycling male germ line stem cell populations, for example, B-Myb or a specific promoter, such as the c-kit promoter region, c-raf-1 promoter, ATM (ataxia-telangiectasia) promoter, vasa promoter, RBM (ribosome binding motif) promoter, DAZ (deleted in azoospermia) promoter, XRCC-1 promoter, HSP 90 (heat shock gene) promoter, cyclin A1 promoter, or FRMI (from fragile X site) promoter, linked to a reporter construct, for example, a construct comprising a gene encoding Green Fluorescent Protein (or EGFP), Yellow Fluorescent Protein, Blue Fluorescent Protein, a phycobiliprotein, such as phycoerythrin or phycocyanin, or any other protein which fluoresces under suitable wave-lengths of light, or encoding a light-emitting protein, such as luciferase or apoaequorin. These unique promoter sequences drive the expression of the reporter construct only during specific stages of male germ cell development, as is known to those skilled in the art. (E.g., Müller, C., et al., *Cloning of the cyclin A1 genomic structure and characterization of the promoter region*, J. Biol. Chem. 276(16): 11220-28 [1999]; Schrans-Stassen, B., H. et al., *Differential expression of c-kit in mouse undifferentiated and differentiating type A spermatogonia*, Endocrinology 140:5894-5900 [1999]). Populations of male germ cells at specific developmental stages, thus, are the only cells in the mixed population which will express the reporter construct(s) and they, thus, can be isolated on this basis. In the case of a fluorescent reporter construct, the cells can be sorted with the aid of, for example, a FACS set at the appropriate wavelength(s), or they can be selected by chemical methods.

Further with respect to the in vitro method of incorporating exogenous genetic material into the genome of a vertebrate, in which male germ cells are obtained from a donor animal and genetically modified in vitro to impart a gene encoding a desired trait or product, male germ cells which exhibit any evidence that the DNA has been modified in the desired manner are isolated or selected, and transferred to the testis of a suitable recipient animal. After transfer, further selection can be attempted after biopsy of one or both of the recipient male's testes, or after examination of the animal's ejaculate amplified by the polymerase chain reaction to confirm whether the desired nucleic acid sequence was actually incorporated. As described above, the initial gene delivery can have included a reporter gene, such as a gene encoding the Green Fluorescent Protein, enhanced Green Fluorescent Protein (EGFP), Yellow Fluorescent Protein, Blue Fluorescent Protein, a phycobiliprotein, such as phycoerythrin or phycocyanin, or any other protein which fluoresces under light of suitable wave-lengths, or encoding a light-emitting protein.

In the in vitro method of incorporating exogenous genetic material into the genome of a vertebrate, the genetically modified germ cells, thus isolated or selected, are preferably transferred to a testis of a recipient male vertebrate, which can be, but need not be, the same donor animal. Before transferring the genetically modified male germ cells to one or more of the testes of the recipient male vertebrate, the testes of the recipient animal are preferably depopulated of native germ cells.

Substantial depopulation of the endogenous male germ cells facilitates the colonization of the recipient testis by the genetically modified germ cells from the donor animal. The depopulation can be done by any suitable means, including by gamma irradiation, by chemical treatment, by means of infectious agents such as viruses, or by autoimmune depletion or by combinations thereof.

Whichever means of depopulating the testis of endogenous male germ cells is used, the basic rigid architecture of the gonad should not be destroyed, nor badly damaged. If there is disruption of the fine system of tubule formation, it may be impossible for the exogenous spermatogonia to repopulate the testis. Disruption of tubules would also presumably lead to impaired transport of testicular sperm and result in infertility. Any controlled testicular injury of this kind should also be limited so that the Sertoli cells are not irreversibly damaged, as they are needed to provide a base for development of the germ cells during maturation. Moreover they may play a role in preventing the host immune defense system from destroying grafted foreign spermatogonia.

But vertebrate testes are most preferably depopulated by a combined treatment of the vertebrate with an alkylating agent and gamma irradiation in accordance with the inventive method of substantially depopulating a vertebrate testes. The method involves a treatment with a cytotoxic alkylating agent, such as, but not limited to, busulfan (1,4-butanediol dimethanesulphonate; Myleran, Glaxo Wellcome), chlorambucil, cyclophosphamide, melphalan, or ethyl ethanesulfonic acid, combined with gamma irradiation, to be administered in either sequence. The combination of a dose of an alkylating agent and a dose of gamma radiation yields unexpectedly superior results in depopulating the testes of germ cells, compared to either treatment alone. The dose of the alkylating agent and the dose of gamma radiation are in an amount sufficient to substantially depopulate the testis.

The preferred dose of alkylating agent is about 4 to 10 milligrams per kilogram of body weight, and about 6 to 8 milligrams per kilogram of body weight is most preferred. The alkylating agent can be administered by any pharmaceutically acceptable delivery system, including but not limited to, intraperitoneal, intravenous, or intramuscular injection, intravenous drip, implant, transdermal or transmucosal delivery systems.

A recovery period between the administration of alkylating agent and irradiation is not essential, and the two treatments are most preferably done within zero to 24 hours of each other. Preferably, the time between the two treatments should not exceed 2 weeks, because this yields less than optimal results for purposes of transferring genetically modified or heterologous male germ cells to recipient testes.

The recipient vertebrate is gamma irradiated with a dose of about 200 to 800 Rads, most preferably about 350 to 450 Rads, directed locally to the testis to be depopulated. Less than 200 Rad yields little effect; greater than 800 Rad commonly produces symptoms of radiation sickness, particularly in the gastrointestinal tract. Within 3 days to 2 months after treatment to depopulate the recipient testis(es) in accordance with the present method, male germ cells can be transferred thereto as described herein. Prior to three days, traces of cytotoxic alkylating agent or endogenous apoptotic signal molecules may remain in the recipient testis to harm the male germ cells transferred thereto. After two months, the endogenous population of male germ cells will typically begin to restablish itself, yielding less than optimal results when transfected, genetically altered, or heterologous male germ cells are transferred to a recipient testes for breeding purposes.

Thus in the in vitro (ex vivo) method, preferably within three days to two months after the final treatment to depopulate the testis(es) of the recipient male vertebrate, the gene delivery mixture is administered to the male germ cells of the donor vertebrate, in vitro, in sufficient amount and under effective conditions such that one or more of them is genetically modified. Genetically modified male germ cells from the donor male vertebrate can then be transferred to the testis(es) of the recipient male such that they lodge in a seminiferous tubule of the testis, where they then mature into genetically modified gametes.

Transferring the isolated or selected genetically modified germ cells into the recipient testis can be accomplished by direct injection using a suitable micropipette. Support cells, such as Leydig or Sertoli cells that provide hormonal stimulus to spermatogonial differentiation, can be transferred to a recipient testis along with the modified germ cells. These transferred support cells can be unmodified, or, alternatively, can themselves have been genetically modified, together with- or separately from the germ cells. These transferred support cells can be autologous or heterologous to either the donor or recipient testis. A preferred concentration of cells in the transfer fluid can easily be established by simple experimentation, but will likely be within the range of about $1 \times 10^5$-$10 \times 10^5$ cells per 10 µl of fluid. This micropipette can be introduced into the vasa efferentia, the rete testis or the seminiferous tubules, optionally with the aid of a picopump to control pressure and/or volume, or this delivery can be done manually. The micropipette employed is in most respects similar to that used for the in vivo injection, except that its tip diameter generally will be about 45 to about 70 microns. The microsurgical method of introduction is similar in all respects to that used for the in vivo method described above. A suitable dyestuff or bubbles (less than 1 mm in diameter) can also be incorporated into the carrier fluid for easy identification of satisfactory delivery of the transfected germ cells to at least one seminiferous tubule of the testis (FIG. 1).

With respect to both the in vivo and in vitro methods of incorporating exogenous genetic material into the genome of a vertebrate involves, breeding the male vertebrate with a female vertebrate of its species means causing the union of male and female gametes so that fertilization occurs and a transgenic zygote is formed; a transgenic progeny or offspring is thereafter produced during gestation of the developing fetus. A union of male and female gametes is brought about by natural mating, i.e., copulation by the male and female vertebrates of the same species, or by in vitro or in vivo artificial means. If artificial means are chosen, then incorporating into the genome a genetic selection marker that is expressed in male germ cells is particularly useful. Preferably expression of the genetic selection marker is regulated from a constitutive or male germ-cell specific promoter, operatively linked to the gene encoding the genetic selection marker.

Artificial means include, but are not limited to, artificial insemination, in vitro fertilization (IVF) and/or other artificial reproductive technologies, such as intracytoplasmic sperm injection (ICSI), subzonal insemination (SUZI), or partial zona dissection (PZD). However, others, such as cloning and embryo transfer, cloning and embryo splitting, and the like, can also be employed.

The thus obtained transgenic vertebrate progeny can, in turn, also be bred, whether by natural mating, artificial insemination, or by in vitro fertilization (IVF) and/or other artificial reproductive technologies, such as intracytoplasmic sperm injection (ICSI), subzonal insemination (SUZI), or partial zona dissection (PZD), to obtain further generations of transgenic progeny. Those skilled in the art will readily appreciate that any desired traits generated as a result of changes to the genetic material of any transgenic animal produced by the inventive method are inheritable. Although the genetic material was originally inserted solely into the germ cells of a parent animal, it will ultimately be present in the germ cells of future progeny and subsequent generations thereof. In addition, the genetic material is also present in cells of the progeny other than germ cells, i.e., somatic cells.

Broadly speaking, a "transgenic" vertebrate is one that has had foreign or exogenous DNA permanently introduced into its cells. The exogenous genes which have been introduced into the animal's cells are called "transgenes" and are xenogeneic and/or allogeneic transgenic genetic material, including biologically functional genetic material. The present invention is applicable to the production of transgenic animals containing xenogeneic, i.e., exogenous DNA from a different species, either in its native, undisturbed form, or in artificially mutated form. In other embodiments, the genetic material is "allogeneic" genetic material, exogenous transgenic material obtained from a different strain, race, breed, or individual of the same species, for example, from an animal having a "normal" form of a gene, or a desirable allele, variant, or mutation thereof. Also the gene can be a hybrid construct consisting of promoter DNA sequences and DNA coding sequences operatively linked together. These sequences can be obtained from different species or DNA sequences from the same species that are not normally juxtaposed. The DNA construct can also contain DNA sequences from prokaryotic organisms, such as bacteria, or from viruses.

The transfected germ cells of the transgenic vertebrate animal preferably have the non-endogenous (exogenous) genetic material integrated into their chromosomes. Those skilled in the art will readily appreciate that any desired traits generated as a result of changes to the genetic material of any transgenic vertebrate produced by this invention are heritable. Although the genetic material was originally inserted solely into the germ cells of a parent animal, it will ultimately be present in the germ cells of direct progeny and subsequent generations thereof. The genetic material is also present in the differentiated cells, i.e. somatic cells, of the progeny.

Included in the invention is a non-human transgenic male vertebrate produced by the in vivo or in vitro method of incorporating exogenous genetic material into the genome of a vertebrate. Produced in accordance with the in vivo method, the transgenic vertebrate is the recipient of the gene delivery mixture. Alternatively, the non-human transgenic male vertebrate is the recipient of the genetically modified male germ cell that was transferred to its testis, in accordance with the in vitro method. The transgenic male vertebrate can be bred with a female of its species, because it comprises a native male germ cell carrying in its genome a polynucleotide of exogenous origin defining a gene encoding a desired trait or product. But somatic cells in tissues outside the testis of the transgenic vertebrate lack the polynucleotide. Preferably, but not necessarily, the transgenic male vertebrate will continue to produce genetically modified gametes for an indefinite period. However, in some embodiments the transgenic state is temporary, lasting for at least several weeks or months, after which non-modified gametes are again exclusively or predominantly produced by the animal.

Also included in the invention is a non-human transgenic vertebrate produced in accordance with the in vivo or in vitro method of incorporating exogenous genetic material into the genome of a vertebrate, wherein the non-human vertebrate is the direct or indirect progeny of the transgenic male vertebrate described above. Thus, this transgenic progeny is the immediate offspring, male or female, of the transgenic male vertebrate or is an offspring thereof separated by one or more generations. The transgenic vertebrate includes one or more cells carrying in their genome a polynucleotide of exogenous origin that encodes a desired trait or product.

Also, the invention includes a transgenic cell derived from the transgenic vertebrate progeny. The cell is a germ cell, such as a spermatozoan or ovum, a precursor germ cell of either of these, or a somatic cell.

Male germ cells are obtained from a male animal's semen, or spermatozoa, spermatogonia, or immature spermatocytes are separated from whole biopsies of testicular tissue containing the male germ cells. Alternatively, male germ line stem cells can be isolated from embryonic tissue. Female germ cells are obtained by known means, including hormonally induced "ripening" and harvesting from the oviducts or aspiration by way of the cervix or by way of a laparoscopic incision.

Somatic cells include stem cells. A stem cell is an undifferentiated mother cell that is self-renewable over the life of the organism and is multipotent, i.e., capable of generating various committed progenitor cells that can develop into fully mature differentiated cell lines. (E.g., T. Zigova and P. R. Sanberg, *The rising star of neural stem cell research*, Nature Biotechnol. 16(11):1007-08 [1998]). All vertebrate tissues arise from stem cells, including hematopoietic stem cells, from which various types of blood cells derive; ectodermal stem cells; neural stem cells, for example, neural progenitors from which brain and nerve tissues derive. Somatic cells also include progenitor cells or terminally differentiated cells of any kind associated with any tissue or organ of the vertebrate body.

Somatic cells are obtained by known sampling or biopsy means from any bodily tissue, organ, or fluid, including but not limited to, blood, heart, kidney, ureter, bladder, urethra, brain, thyroid, parotid gland, pancreas, hypothalamus, pituitary gland, submaxillary gland, sublingual gland, lymph node, bone, bone marrow, cartilage, lung, mediastinum, breast, uterus, ovary, testis, prostate, cervix uteri, endometrium, liver, spleen, adrenal, esophagus, stomach, intestine, hair root, muscle, nerve, urine, amniotic fluid, chorionic villus, skin, vascular or oral epithelium, or spinal fluid. The inventive transgenic cells can be cultured or stored by well known means.

The invention also relates to vertebrate semen containing a plurality of the inventive transgenic male germ cell. The inventive vertebrate semen is useful for breeding or other suitable purposes. The semen is obtained from ejaculate produced by the inventive transgenic male vertebrate or its transgenic male progeny (either immediate progeny or progeny separated by one or more generations), and methods of inducing ejaculation by a male vertebrate and capturing the semen are well known. The semen can be processed, e.g., by washing, and/or stored by means such as are known in the art. For example, storage conditions include the use of cryopreservation using programmed freezing methods and/or the use of cryoprotectants, for example, dimethyl sulfoxide (DMSO), glycerol, trehalose, or propanediol-sucrose, and the use of storage in substances such as liquid nitrogen.

Such storage techniques are particularly beneficial to young adult humans or children, undergoing oncological treatments for such diseases such as leukemia or Hodgkin's lymphoma. These treatments frequently irreversibly damage the testicle and, thus, render it unable to recommence spermatogenesis after therapy by, for example, irradiation or chemotherapy. In species other than humans, the present techniques are valuable for transport of gametes as frozen germ cells. Such transport will facilitate the establishment of various valued livestock or fowl lines, at a remote distance from the donor animal. This approach is also applicable to the preservation of endangered species across the globe.

Thus, the invention is also includes a method of producing a non-human transgenic vertebrate animal line, the individuals of which comprise native germ cells carrying in their genome at least one xenogeneic polynucleotide. The transgenic vertebrates bred with other transgenic or non-transgenic animals of the same species will produce some transgenic progeny, including fertile individuals. The method involves breeding of the fertile transgenic progeny with a member of the opposite sex of the same species as described above; and selecting its progeny for the presence of the polynucleotide. The inventive method of producing a non-human transgenic vertebrate animal line is simple and efficient, and is more easily accomplished in large mammals than in mice because of the larger size of the testicular ducts. Far fewer animals are needed to produce transgenic progeny by genetic modification of male germ cells, which can be produced continually from repeated mating without interruption by pregnancy or parturition. It requires no expensive equipment, nor the training necessary for microinjection.

The inventive technology is applicable to the field of gene therapy, since it permits the introduction of genetic material encoding and regulating specific genetic traits. Thus, in the human, for example, by treating parents it is possible to correct many single gene disorders which otherwise might affect their children. It is similarly possible to alter the expression of fully inheritable disorders or those disorders having at least a partially inherited basis, which are caused by interaction of more than one gene, or those which are more prevalent because of the contribution of multiple genes. This technology can also be applied in a similar way to correct disorders in animals other than human primates. In some instances, it may be necessary to introduce one or more "gene(s)" into the germ cells of the animal to attain a desired therapeutic effect, as in the case where multiple genes are involved in the expression or suppression of a defined trait. In the human, examples of multigenic disorders include diabetes mellitus caused by deficient production of, or response to, insulin, inflammatory bowel disease, certain forms of atheromatous cardiovascular disease and hypertension, schizophrenia and some forms of chronic depressive disorders, among others. In some cases, one gene can encode an expressible product, whereas another gene encodes a regulatory function, as is known in the art. Other examples are those where homologous recombinant methods are applied to repair point mutations or deletions in the genome, inactivation of a gene causing pathogenesis or disease, or insertion of a gene that is expressed in a dominant negative manner, or alterations of regulating elements such as gene promoters, enhancers, the untranslated tail region of a gene, or regulation of expansion of repeated sequences of DNA which cause such diseases as Huntingdon's chorea, Fragile-X syndrome and the like.

A specific reproductive application of the present invention is to the treatment of animals, particularly humans, with disorders of spermatogenesis. Defective spermatogenesis or spermiogenesis frequently has a genetic basis, that is, one or mutations in the genome can result in failure of production of normal sperm cells. This can happen at various stages of the development of germ cells, and may result in male infertility or sterility. The present invention is applicable, for example, to the insertion or incorporation of nucleic acid sequences into a recipient's genome and, thereby, establish spermatogenesis in the correction of oligozoospermia or azoospermia in the treatment of infertility. Similarly, the present methods are also applicable to males whose subfertility or sterility is due to a motility disorder with a genetic basis.

The present invention is additionally applicable to the generation of transgenic animals expressing agents which are of therapeutic benefit for use in human and veterinary medicine or well being. Examples include the production of pharmaceuticals in domestic cows' milk, such as factors which enhance blood clotting for patients with types of haemophilia, or hormonal agents such as insulin and other peptide hormones.

The present method is further applicable to the generation of transgenic animals, for example pigs, of a suitable anatomical and physiological phenotype for human xenograft transplantation. The inventive transgenic technology permits the generation of animals which are immune-compatible with a human recipient. Appropriate organs, for example, can be removed from such animals to allow the transplantation of, for example, the heart, lung and kidney.

In addition, male germ cells genetically modified in accordance with this invention can be obtained from the transgenic animal, and stored under conditions effective for later use, as is known in the art.

The invention will now be described in greater detail by reference to the following non-limiting examples. The pertinent portions of the contents of all references, and published patent applications cited throughout this patent necessary for enablement purposes are hereby incorporated by reference.

EXAMPLES

Genetic Modification of Male Germ Cells In Vivo and In Vitro

In Vivo Adenovirus-Enhanced Transferrin-Polylysine-Mediated Delivery of Green Lantern Reporter Gene Delivery System to Testicular Cells The adenovirus enhanced transferrin-polylysine-mediated gene delivery system has been described and patented by Curiel et al. (Curiel D. T.,et al., Adenovirus enhancement of transferrin-polylysine-mediated gene delivery, PNAS USA 88: 8850-8854 (1991). The delivery of DNA depends upon endocytosis mediated by the transferrin receptor (Wagner et al., Transferrin-polycation conjugates as carriers for DNA uptake into cells, PNAS (USA) 87: 3410-3414 (1990). In addition this method relies on the capacity of adenoviruses to disrupt cell vesicles, such as endosomes and release the contents entrapped therein. This system can enhance the gene delivery to mammalian cells by as much as 2,000 fold over other methods.

The gene delivery system employed for the in vivo experiments was prepared as shown in examples below.

Example 1

Preparation of Transferrin-Poly-L-Lysine Complexes

Human transferrin was conjugated to poly (L-lysine) using EDC (1-ethyl-3-(3-dimethyl aminopropyl carbodiimide hydrochloride) (Pierce), according to the method of Gabarek and Gergely (Gabarek & Gergely, Zero-length cross-linking procedure with the use of active esters, Analyt. Biochem 185:131 (1990)). In this reaction, EDC reacts with a carboxyl group of human transferrin to form an amine-reactive intermediate. The activated protein was allowed to react with the poly (L-lysine) moiety for 2 hrs at room temperature, and the reaction was quenched by adding hydroxylamine to a final concentration of 10 mM. The conjugate was purified by gel filtration, and stored at −20° C.

Example 2

Preparation of DNA for in Vivo Transfection

The Green Lantern-1 vector (Life Technologies, Gibco BRL, Gaithersberg, Md.) is a reporter construct used for monitoring gene transfection in mammalian cells. It consists of the gene encoding the Green Fluorescent Protein (GFP) driven by the cytomegalovirus (CMV) immediate early promoter. Downstream of the gene is a SV40 polyadenylation signal. Cells transfected with Green Lantern-1 fluoresce with a bright green light when illuminated with blue light. The excitation peak is 490 nm.

Example 3

Preparation of Adenoviral Particles

Adenovirus dl312, areplication-incompetent strain deleted in the Ela region, was propagated in the Ela trans-complementing cell line 293 as described by Jones and Shenk (Jones and Shenk, PNAS USA (1979) 79: 3665-3669). A large scale preparation of the virus was made using the method of Mittereder and Trapnell (Mittereder et al., "Evaluation of the concentration and bioactivity of adenovirus vectors for gene therapy", J. Urology, 70: 7498-7509 (1996)). The virion concentration was determined by UV spectroscopy, 1 absorbance unit being equivalent to 10 viral particles/ml. The purified virus was stored at −70° C.

Example 4

Formation of Transferrin-Poly-L Lysine-DNA-Viral Complexes

Six (6) micrograms of transferrin-polylysine complex from Example 1 were mixed in $7.3 \times 10^7$ adenovirus dl312 particles prepared as in Example 3, and then mixed with 5 µg of the Green Lantern DNA construct of Example 2, and allowed to stand at room temperature for 1 hour. About 100 µl of the mixture were drawn up into a micropipette, drawn on a pipette puller, and slightly bent on a microforge. The filled micropipette was then attached to a picopump (Eppendorf), and the DNA complexes were delivered under continuous pressure, in vivo to mice as described in Example 6.

Controls were run following the same procedure, but omitting the transferrin-poly-lysine-DNA-viral complexes from the administered mixture.

Example 5

Comparison of Adenovirus-Enhanced Transferrin-Polylysine & Lipofectin Mediated Transfection Efficiency The conjugated adenovirus particle complexed with DNA were tested on CHO cells in vitro prior to in vivo testing. For these experiments a luciferase reporter gene was used due to the ease of quantifying luciferase activity. The expression construct consists of a reporter gene encoding luciferase, is driven by the CMV promoter (Invitrogen, Carlsbad, Calif. 92008). CHO cells were grown in Dulbecco's modified Eagle's medium (DMEM) with 10% fetal calf serum. For gene transfer experiments CHO cells were seeded into 6 cm tissue culture plates and grown to about 50% confluency ($5 \times 10^5$ cells). Prior to transfection the medium was aspirated and replaced with serum free DMEM. Cells were either transfected with transferrin-polylysine-DNA complexes or with lipofectin DNA aggregates. For the transferrin-polylysine mediated DNA transfer, the DNA-adenovirus complexes were added to the cells at a concentration of 0.05-$3.2 \times 10^4$ adenovirus particles per cell. Plates were returned to the 5% $CO_2$ incubator for 1 hour at 37° C. After 1 hour 3 ml of complete media was added to the wells and the cells were allowed to incubate for 48 hours before harvesting. The cells were removed from the plate, counted and then lysed for measurement of luciferase activity.

For cells transfected by lipofectin, 1 µg of CMV-luciferase DNA was incubated with 17 µl of Lipofectin (Life Technologies). The DNA-lipofectin aggregates were added to the CHO cells and allowed to incubate at 37° C. at 5% $CO_2$ for 4 hours. Three milliliters of complete medium was added then to the cells and they were allowed to incubate for 48 hours. The cells were harvested, counted and lysed for luciferase activity. The luciferase activity was measured by a luminometer. The results obtained are shown in Table 1.

The data included in Table 1 below show that the adenovirus-enhanced transferrin-polylysine gene delivery system is 1,808 fold more efficient than lipofection for transfection of CHO cells.

TABLE 1

Comparison of Lipofection & Adenovirus Enhanced Transferrin-polylysine Transfection of CHO Cells

| Sample | Treatment | Luciferase Activity (RLU) |
|---|---|---|
| 1 | $1 \times 10^7$ particles + 6 ug CMV-Luc | 486 |
| 2 | $2.5 \times 10^7$ particles + 6 ug CMV-Luc | 1201 |
| 3 | $5.0 \times 10^7$ particles + 6 ug CMV-luc | 11119 |
| 4 | $1 \times 10^9$ particles + 6 ug CMV-Luc | 2003503 |
| 5 | Lipofection | 1108 |
| 6 | Unmanipulated cells | 155 |

Example 6

In Vivo Delivery of DNA to Animal's Germ Cells via Transferrin-L-lysine-DNA-Viral Complexes The GFP DNA-transferrin-polylysine viral complexes, prepared as described in Example 4 above, were delivered into the seminiferous tubules of three (3)-week-old B6D2F1 male mice. The DNA delivery by transferrin receptor-mediated endocytosis is described by Schmidt et al. and Wagner et al. (Schmidt et al., Cell 4: 41-51 (1986); Wagner, E., et al. *PNAS* (1990), (USA) 81: 3410-3414 [1990]). In addition, this delivery system relies on the capacity of adenoviruses to disrupt cell vesicles, such as endosomes and release the contents entrapped therein. The transfection efficiency of this system is almost 2,000 fold higher than lipofection.

The male mice were anesthetized with 2% Avertin (100% Avertin comprises 10 g 2,2,2-tribromoethanol (Aldrich) and 10 ml t-amyl alcohol (Sigma), and a small incision made in their skin and body wall, on the ventral side of the body at the level of the hind leg. The animal's testis was pulled out through the opening by grasping at the testis fat pad with forceps, and the vas efferens tubules exposed and supported by a glass syringe. The GFP DNA-transferrin-polylysine viral complexes were injected into a single vasa efferentia using a glass micropipette attached to a hand held glass syringe or a pressurized automatic pipettor (Eppendorf), and Trypan blue added to visualize the entry of the mixture into the seminiferous tubules. The testes were then placed back in the body cavity, the body wall was sutured, the skin closed with wound clips, and the animal allowed to recover on a warm pad.

Example 7

Detection of DNA and Transcribed Message

Nine (9) days after delivery of the genetic material to the animals' testis, two of the animals were sacrificed, their testes removed, cut in half, and frozen in liquid nitrogen. The DNA from one half of the tissues, and the RNA from the other half of the tissues were extracted and analyzed.

(a) Detection of DNA

The presence of GFP DNA in the extracts was tested 9 days after administration of the transfection mixture using the polymerase chain reaction, and GFP specific oligonucleotides. GFP DNA was present in the testes of the animals that had received the DNA complexes, but was absent from sham operated animals.

(b) Detection of RNA

The presence of GFP mRNA was assayed in the testes of experimental animals as follows. RNA was extracted from injected, and non-injected testes, and the presence of the GFP messages was detected using reverse transcriptase PCR(RT PCR) with GFP specific primers. The GFP message was present in the injected testes, but not in the control testes. The DNA detected above by PCR analysis is episomal GFP DNA. The transfected gene was being transiently expressed.

Example 8

Expression of Non-Endogenous DNA

Two males, one having received an injection with the GFP transfection mixture and a control to whom only surgery was administered, were sacrificed 4 days after injection, and their testes excised, and fixed in 4% paraformaldehyde for 18 hours at 4° C. The fixed testis was then placed in 30% sucrose in PBS with 2 mM $MgCl_2$ for 18 hours at 4° C., embedded in OCT frozen on dry ice, and sectioned. When the testes of both animals were examined with a confocal microscope with fluorescent light at a wavelength of 488 nM, bright fluorescence was detected in the tubules of the GFP-injected mice, but not in the testes of the controls. Many cells within the seminferous tubules of the GFP-injected mouse showed bright fluorescence, which evidences that they were expressing Fluorescent Green Protein.

Example 9

Generation of Offspring from Normal Matings

GFP transfected males were mated with normal females. The females were allowed to complete gestation, and the pups to be born. The pups (F1 offspring or progeny) were screened for the presence of the novel genetic material(s).

Example 10

In Vitro Transfection of Testicular Cells

Cells were isolated from the testes of three 10-day-old mice. The testes were decapsulated and the seminiferous tubules were teased apart and minced with sterile needles. The cells were incubated in enzyme mixture for 20 minutes at 37° C. The enzyme mixture was made up of 10 mg bovine serum albumin (embryo tested), 50 mg bovine pancreatic trypsin type III, Clostridium collagenase type I, 1 mg bovine pancreatic DNAse type I in 10 mls of modified HTF medium (Irvine Scientific, Irvine, Calif.). The enzymes were obtained from Sigma Company (St. Louis, Mo. 63178). After digestion, the cells were washed twice by centrifugation at 500×g with HTF medium and resuspended in 250 µl HTF medium. The cells were counted, and $0.5 \times 10^6$ cells were plated in a 60 mm culture dish in a total volume of 5 ml DMEM (Gibco-BRL, Life Technologies, Gaithesburg, Md. 20884). A transfection mixture was prepared by mixing 5 µg Green Lantern DNA (Gibco-BRL, Life Technologies, Gaithesburg, Md. 20884) with 20 µl Superfect (Qiagen, Santa Clarita, Calif. 91355) and 150 µl DMEM. The transfection mix was added to the cells and they were allowed to incubate for 3 hours at 37° C., 5% $CO_2$ The cells were transferred to a 33° C. incubator and incubated overnight.

The following morning the cells were assessed for transfection efficiency by counting the number of fluorescent cells. In this experiment the transfection efficiency was 90% (Figure not shown). The testicular cells transfected with Green Lantern viewed with Nomaski optics x20 show the same cells viewed with FITC. Nearly all the cells were fluorescent, which is confirmation of their successful transfection.

Example 11

Preparation of a Cell Suspension from Testicular Tissue for Cryopreservation

A cell suspension was prepared from mice of different ages as described below.

Group I: 7-10 day olds

Group II: 15-17 day olds

Group III: 24-26 day olds

The mice's testes were dissected, placed in phosphate buffered saline (PBS) decapsulated, and the seminiferous tubules were teased apart. Seminiferous tubules from groups I and II were transferred to HEPES buffered culture medium (D-MEM) (Gibco-BRL, Life Technologies, Gaithersberg, Md. 20884) containing 1 mg/ml Bovine serum albumin (BSA) (Sigma, St. Louis, Mo. 63178) and Collagenase Type I (Sigma) for the removal of interstitial cells. After a 10 minute incubation at 33° C., the tubules were lifted into fresh culture medium. This enzymatic digestion was not carried out on the testes from group I because of their fragility.

The tubules from group II and III mice or the whole tissue from group I mice were transferred to a Petri dish with culture medium and were cut into 0.1-1 mm pieces using a sterile scalpel and needle. The minced tissue was centrifuged at 500×g for 5 minutes and the pellet was resuspended in 1 ml of enzyme mix. The enzyme mix was made up in D-DMEM with HEPES (Gibco-BRL) and consisted of 1 mg/ml bovine serum albumin (BSA) (Sigma, embryo tested), 1 mg/ml collagenase I (Sigma) and 5 mg/ml bovine pancreatic trypsin (Sigma) and 0.1 mg/ml deoxyribonuclease I (DN-EP, Sigma). The tubules were incubated in enzyme mix for 30 minutes at 33° C. After the incubation, 1 ml of medium was added to the mix and the cells were centrifuged at 500×g for 5 min. The cells were washed twice in medium by centrifugation and resuspension. After the final wash the cell pellet was resuspended in 250 µl of culture medium and counted.

Example 12

Transferring Transfected Male Germ Cells Into Recipient Testis

The cells were injected into the testis via the vasa efferentia using a micropipette. $3\times10^5$ cells in a total volume of 50 µl were used for the injection. The cells were mixed with Trypan blue prior to the injection. The recipient mice were anesthetized with 0.017 mL/g body wt. Avertin. An incision was made across the lower abdominal wall and the testis was gently pulled to the exterior through the incision by pulling on the fat pad associated with the testis. The vas efferens was exposed and approximately 20 µL of cell suspension was injected into the vas efferens using a glass micropipette held in a steel micropipette holder (Leitz). The cells were expelled from the pipette using air pressure from a 20 mL glass syringe. Prior to the transfer of transfected germ cells to the recipient animals, the recipient testes were depopulated of endogenous male germ cells.

Example 13

Depopulating the Recipient Testis of Male Germ Cells

Comparison of Depopulating Treatments. Eight-week-old C57BL/6J mice were allowed to acclimatize for a few days and then were assigned to one of the following three treatment groups. They received: (1) 400 Rad gamma irradiation; (2) 4 µg/g body weight of busulfan (1,4-butanediol dimethanesulphonate; Myleran, Glaxo Wellcome); or (3) a combination treatment of busulfan (4 µg/g body wt) followed one week later by 400 Rad of gamma irradiation ("busulfan/400 Rad" treatment). A fourth group of untreated C57BL/6J mice of the same age as the treatment groups was used as a control. There were 24 mice in each treatment group, and 3 mice were sacrificed at each of the following time intervals after treatment: 5 hours, 24 hours, 48 hours, 72 hours, 1 week, 2 weeks, 1 month and 2 months after treatment.

In addition, other C57BL/6J mice receiving the combined busulfan/400 Rad treatment were examined histologically at time points up to five months after treatment (the testes of these other mice were fixed overnight in 4% paraformaldehyde in PBS, pH 7.4 at 4° C., dehydrated and embedded in paraffin before sectioning and H&E staining).

Delivery of an Alkylating Agent to Recipient Vertebrates. The male mice receiving busulfan received a dose of 4 µg busulfan per g body wt. The busulfan was first dissolved 8 mg/mL in 100% dimethyl sulfoxide (DMSO) then, immediately before injection, was diluted 1:1 in phosphate buffered saline, pH 7.4. The mice were injected with the diluted busulfan solution intraperitoneally.

Irradiation Treatment of Recipient Vertebrates. For the gamma irradiation treatment, mice were anesthetized with 0.017 mL/g body wt. of 2.5% Avertin. Gamma irradiation was specifically directed to the testis in the following manner. Each mouse was placed in a lead chamber with only the testis and lower abdomen exposed through elliptical holes to the irradiating source ($^{137}$Cs Gammacell 40 irradiator [Nordion]). There were six aligned holes in the floor and roof of the chamber through which the gamma radiation passed unobstructed. After irradiation the animals were allowed to recover from the anesthesia on a warm heating pad or water bed until they regained consciousness.

Histology. At selected time points, mice from each treatment group were euthanized, and testicular tissues to be examined were fixed in 10% formalin in PBS, pH 7.4, at 4° C. for 24 hours. Small slits in the testis capsule were made to allow penetration of the fixative. Fixed samples were washed four times with PBS, and embedded in paraffin using a Tissue Tek-II tissue processor (MET). Sections of 8 µm thickness were cut, stained with haemotoxylin and eosin (H&E), and mounted with Aquamount (Lerner Laboratories) on glass slides with coverslips. The sections were viewed on a Zeiss or Olympic light microscope with a 40× objective lens (total magnification 400×).

Quantitative Histologic Analysis. Quantitative data were collected from the testes of two animals for each of the treatment groups at two months after treatment. (Table 2). For the control group only one mouse was used. The seminiferous tubules in a single section were counted using a 5× objective on a Zeiss light microscope (50× total magnification). Individual seminiferous tubules were examined at 400× total magnification. Seminiferous tubules were considered severely damaged if hardly any cells remained in the tubule, and the tubule consisted of a basement membrane with a single layer of cells, mostly spermatogonia, lying along the basement membrane. Moderately damaged tubules were tubules, in which some of the spermatogenic layers close to the lumen were partially sloughed off. Spermatozoan heads were counted in the tubules and averaged over the total number of tubules counted.

Results of Histological Analysis. Obvious histological changes were not seen in the testis until two weeks after treatment. (Data no shown). After two weeks changes included severe disruption of spermatogenesis; all the mature spermatozoa were lost and no spermatids or spermatocytes were present. A few Sertoli cell nuclei and spermatogonia were detectable in the periphery along the basement membrane. Six weeks after busulfan/400 Rad treatment there was evidence of the re-establishment of spermatogenesis. Some spermatids and spermatozoa were seen as well as a few spermatocytes.

By about 3 months most of the seminiferous tubules had at least partially recovered and all stages of spermatogenesis appear to be represented. (Data not shown). Spermatogenesis had returned to normal at this stage by five months after busulfan/400 Rad treatment.

The three treatment groups described above were also compared. The most dramatic differences among the groups were seen at two months after treatment. At two months the mice that were treated with the combined busulfan/400 Rad gamma irradiation treatment showed the greatest number of substantially depopulated seminiferous tubules. Seminiferous tubules from this group also contained a smaller average number of sperm heads per seminiferous tubule and the greatest proportion of severely and moderately damaged seminiferous tubules compared to the other treatment groups and the control mice. (Table 2). Treatment of the mice with either 400 Rad gamma irradiation or busulfan alone also resulted in damage to the spermatogenic process, including sloughing of cells into the lumen of the tubule, and substantially fewer mature spermatozoan heads compared to the controls, but to a significantly lesser extent than exemplified by the busulfan/400 Rad treatment group.

These results clearly demonstrate that a combination of treatment with an alkylating agent and gamma irradiation is a more effective method of depopulating a vertebrate testis of male germ cells than either of the two treatments alone.

TABLE 2

Comparison of Various Methods of Depopulating a Vertebrate Testis of Male Germ Cells.

| Treatment | No. Tubules Counted | No. Severely damaged | No. Moderately damaged | Total No. Sperm heads | Average No. sperm heads/tubule |
|---|---|---|---|---|---|
| Control | 50 | 0 | 0 | 1733 in 50 tubules | 35 |
| Busulfan/400R | 50 | 15 (30%) | 3 (6%) | 460 in 50 tubules | 9 |
| Busulfan/400R | 57 | 14 (24%) | 8 (14%) | 383 in 50 tubules | 8 |
| Busulfan | 70 | 1 (1%) | 5 (7%) | 957 in 50 tubules | 19 |
| Busulfan | 69 | 3 (10%) | 2 (3%) | 764 in 50 tubules | 15 |
| 400R | 52 | 2 (4%) | 1 (2%) | 1005 in 50 tubules | 20 |
| 400R | 41 | 2 (5%) | 3 (7%) | 827 in 41 tubules | 20 |

Example 14

In vivo Transduction Using a Viral Vector

A retroviral vector was used to transduce (genetically alter or modify) male germ cells of mice in vivo. Specifically, a pseudo-typed HIV-derived viral vector (L. Naldini et al., *In vivo gene delivery and stable transduction of nondividing cells by a Lentiviral vector*, Science 272:263-67 [1996]), was used, as modified by Carlos Lois to express Green Flourescent Protein (GFP) instead of the LacZ reporter gene, under the transcriptional control of the CMV promoter (HR'GFP).

Recipient C57BL/6J mice were treated with busulfan 44 days prior to viral infection. C57BL/6J male mice were injected intraperitoneally with 0.1 ml busulfan at a concentration of 1 mg/ml. The dose was 4 µg busulfan/gm body wt.

One pretreated mouse was anesthetized with Avertin (0.017 mls/gm body wt.), and a ventral midline incision was made and the right testis exposed.

The vas efferentia were dissected away from the fat, and ten microlitres of HIV-derived GFP vector, HR'GFP, at a titer of $1 \times 10^9$ particles/ml were injected into the seminiferous tubules of the right testis via the vas efferens of a busulfan-treated C57 BL/6J mouse. Injection was done with a quartz glass micropipette attached to a Picospritzer II. The Picospritzer was set at 80 psi and gave 1 second bursts upon manual depression of a foot pedal. All the seminiferous tubules of the testis can be reached with a single injection as the vas efferens leads to a common chamber, the rete testis, from which all the tubules radiate. The left testis was not injected and was used as a control. Transduction of the testicular cells within the tubules was widespread.

Twenty one days after infection, the mouse was sacrificed and the testes were fixed overnight in 4% paraformaldehyde in PBS, pH 7.4 at 4° C. The testes were washed three times in PBS and placed in 20% sucrose overnight at 4° C. The testes were frozen in OCT and sectioned at 8 µm on a cryostat. The sections were thawed to room temperature immersed in phosphate saline buffer and viewed on a Zeiss 310 confocal microscope. The laser was set at a wavelength of 488 nm.

Green fluorescence was seen in all the seminiferous tubules that were viewed, although the intensity was greatest in the tubules at the surface of the testis. Transduction was seen in the Sertoli support cells as well as in the spermatogonia along the basement membrane, but little was seen in the spermatocytes or spermatids. Very few mature spermatozoa were present due to the Busulfan treatment. No fluorescence was seen in the left testes used as control. This shows that male germ cells can be transduced by a viral vector and that the transduced gene is expressed.

Example 15

Optimization Microinjection of Gene Delivery Mixture through the Vas Efferens

The method of delivery (Winston, R. M. L., *Microsurgical reanastomosis of the rabbit oviduct and its functional and pathological sequelae*, Brit. J. Obstet. Gynaecol. 82:513-522 ([1975]) of viral particles into a single vas efferens, and thence to the seminiferous tubules, was first optimized in several mice (FIGS. 1a-1d). The mice were treated with busulfan (Myleran: Glaxo Wellcome) 14 days before microsurgery to maximize the chance of viral particles gaining access to spermatogonia, which lie on the basement lamella of the tubules. Busulfan, an alkylating cytotoxic agent, depopulates the testis (Bucci, L. and Meistrich, M., *Effects of busulfan on murine spermatogenesis: cytotoxicity, sterility, sperm abnormalities, and dominant lethal mutations*, Mut. Res. 176:259-268 [1987]). At the intraperitoneal (IP) dose given (4 µg/g body wt.) many of the spermatocytes, spermatids and spermatozoa were eliminated from the tubules, but the testis recovered three to four months afterward and fertility was restored. This implies that stem cells remain viable and can repopulate the testis. Stem cell spermatogonia are known to be resistant to insults, often surviving when other germ cell types are destroyed (Huckins, C. & Oakberg, W. F., *Morphological and quantitative analysis of spermatogonia in mouse testes using whole mounted seminiferous tubules. II. The irradiated testes*, Anat. Rec. 192:529-42 [1978]).

Example 16

Figure 1B:
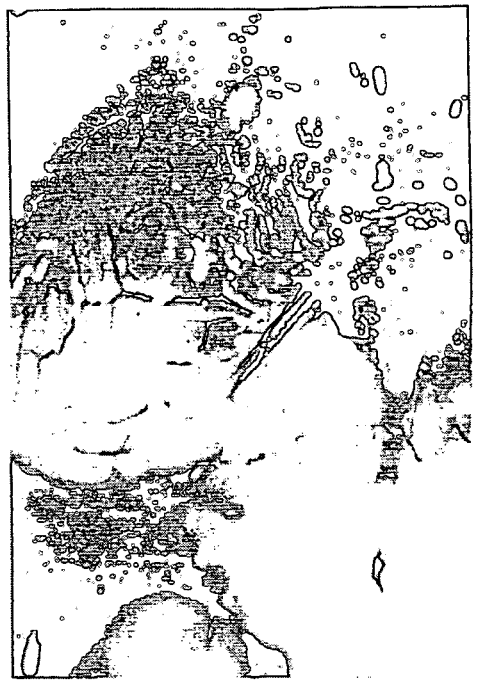
FIG. 1(b) shows a vas efferens supported by a pipette tip, 1 mm diameter.
Figure 1C:
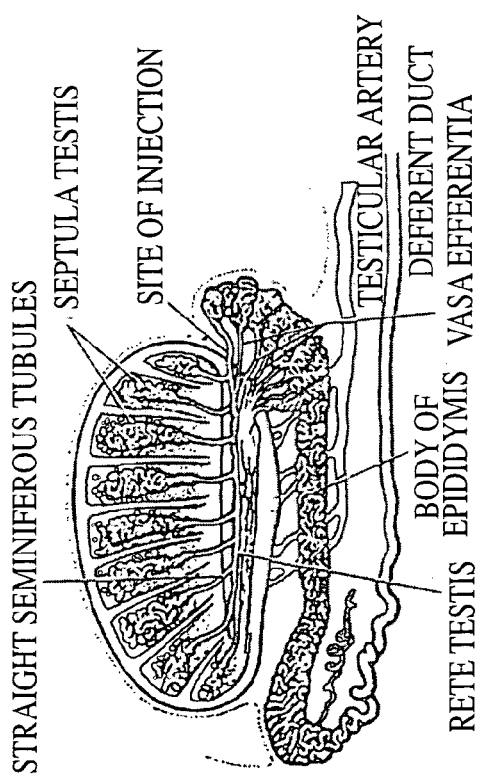
FIG. 1(c) shows a mouse testis perfused with bromophenol blue after being injected in the vas efferens.
Figure 1D:
FIG. 1(d) shows air bubbles in the testis, confirming satisfactory delivery of viral particles.

Production of Transgenic Progeny by In Vivo Transduction of Male Germ Cells Followed by Natural Matins Microsurgery. After depopulation of the testis as described in Example 15, viral particles were delivered to the seminiferous tubules as follows: Mice were anaesthetised with isofluorane (0.5-2% in oxygen). Each testis was exposed through a midline abdominal incision. Using a microsurgical approach (Winston [1975]; Zeiss microscope at magnification 4 to 50×) the tissue bundle containing the vasa efferentia was visualised (FIG. 1a-1b). Dissection from the surrounding fat was aided by a stream of phosphate buffered saline forced through a fine needle. A quartz glass micropipette was back-filled with 10 μL viral particles ($10^9$ pfu/ml) mixed with 1 μL polybrene (80 mg/mL). This was attached to a micropipette (Eppendorf) and the particles introduced into the vas efferens under 2.2 bar pressure in pulses of 1.5 seconds, controlled by foot pedal. Earlier trials using 1% Bromophenol dye showed that most seminiferous tubules could be filled (FIG. 1c), but during treatments, no dye was used and small air bubbles were introduced into the liquid containing viral particles to confirm dispersion into the seminiferous tubules (FIG. 1d). To preserve fertility, only single vasa efferentia were injected, reducing injury to the remaining ducts.

Preparation of the Viral Vector. The plasmid, pHR'-CMV-LacZ (L. Naldini et al. [1996]), was modified by replacing the BamHI-XhoI fragment containing the LacZ gene with a fragment containing the EGFP gene ('humanised' GFP, Clontech). For the production of viral particles 40 μg plasmid DNA was used to transfect a 10-cm plate of 293T cells. The 40 μg of plasmid DNA was made up of 10 μg pCMV R9, 20 μg of modified pHR' and 10 μg envelope plasmid. Vesicular-stomatitis-virus-glycoprotein (VSV-G) pseudotyped vectors were produced by contransfection of the vector plasmid with the Moloney murine leukemia virus (MLV) gag-pol packaging plasmid pCMV-GAGPOL and the VSV-G plasmid. The supernatant was harvested 48-60 hours after transfection, subjected to high speed centrifugation, filtered through 0.45 μm filters and assayed. The transducing viral particles had the MLV restricted envelope protein, env, substituted with a broad-spectrum env protein from the vesicular stomatitis virus.

In Vivo Transduction of Male Germ Cells. Six mice were now treated with viral particles containing the transducing vector pHR' ($10^9$ particles/mL). A single vas efferens was injected with a volume of 10 μL retroviral concentrate together with 1 μL (80 mg/mL) polybrene. After 24 days the mice were sacrificed and the testes removed and fixed for cryosectioning and histological examination. Testes were fixed for 48 hours in 4% Paraformaldehyde pH 7.4, and placed in 20% sucrose in phosphate saline buffer pH 7.4 at 4° C. for 24 hours. They were embedded in OCT and stored at −70° C. They were cryosectioned at 8 μm and viewed in a Zeiss 410 confocal microscope (FIG. 2).

Figure 2B:
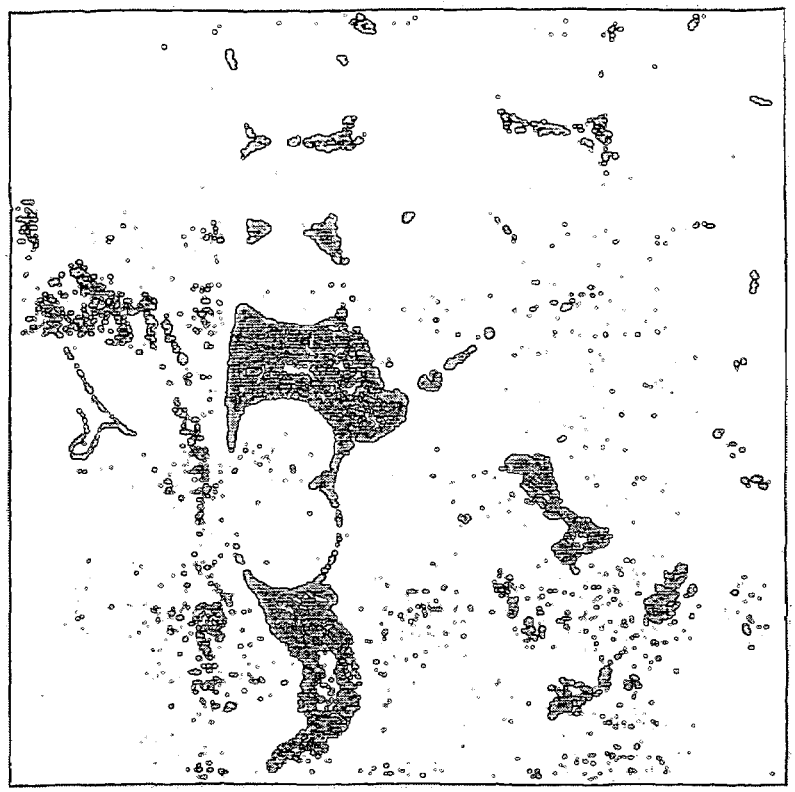
FIG. 2(b) shows transduced spermatogonia; GFP expression is visible in the cytoplasm surrounding large dark nuclei.
Figure 2A:
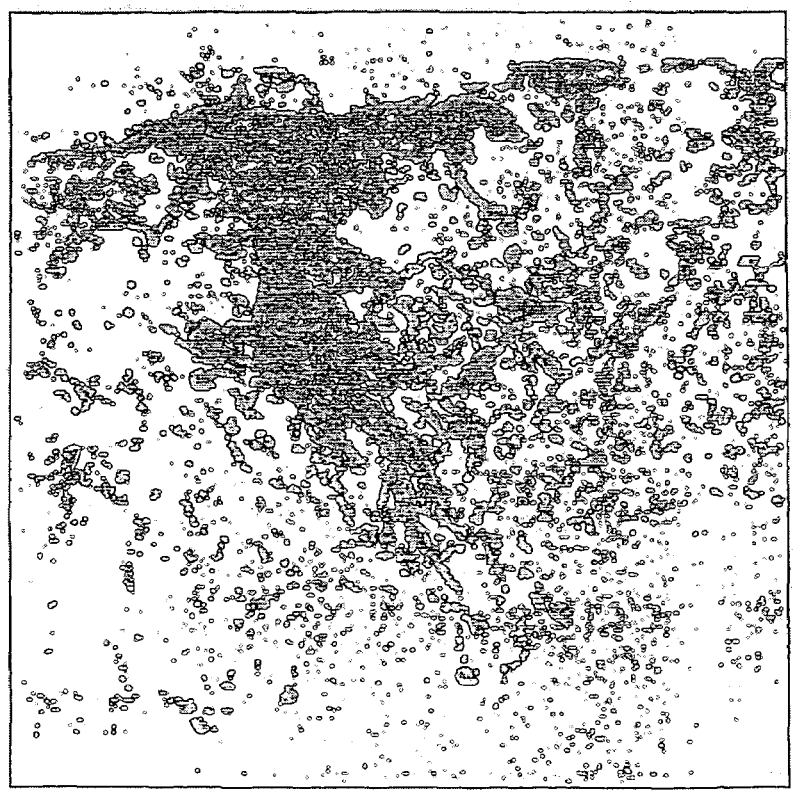
FIG. 2(a) shows a transduced Sertoli cell expressing GFP.

Nearly all tubules sectioned contained cells expressing GFP. Expression was highest in Sertoli and spermatogonia cells (FIGS. 2a-b).

Natural Matings with Females after Transduction of Male Germ Cells. Eleven C57/B1/6J young males were then selected to test whether transduced male germ cells could transmit the retrovirally integrated transgene to the next generation. Six of these mice were treated with a bolus of busulfan (IP; 4 μg/gm body wt.) 14 days before in vivo transduction microsurgery in accordance with the in vivo method of incorporating exogenous genetic material into the genome of a vertebrate, as described above, and three received the same dose only one week before in vivo transduction. Two other mice were not pre-treated with busulfan before the in vivo transduction operation. Lentiviral particles were introduced into the seminiferous tubules. After 14 weeks, B6D2F1 females were introduced into cages with the males. Transduced males fathered at least two successive litters. Litters were conceived 14, 15, 19 and 20 weeks after transduction. All the males, except one dying immediately after surgery, fathered transgenic offspring. (Table 3).

TABLE 3

Production of transgenic offspring per litter fathered by treated males at various times after mating.

| Mouse # | Pre-treatment | 14 weeks | 15 weeks | 19 weeks | 20 weeks |
|---|---|---|---|---|---|
| 1 | Busulfan 1 week | — | 2/9 (22%) | 8/10 (90%) | 0/9 (0%) |
| 2 | Busulfan 1 week | — | 1/7 (14%) | 1/7 (14%) | 2/7 (28%) |
| 3 | Busulfan 1 week | 4/7 (57%) | 1/8 (12%) | 4/6 (66%) | 0/7 (0%) |
| 4 | Busulfan 1 week | 7/8 (87%) | 3/7 (43%) | 1/6 (17%) | 1/8 (12%) |
| 5 | Busulfan 2 weeks | 5/6 (83%) | 8/9 (89%) | — | 0/8 (0%) |
| 6 | Busulfan 2 weeks | — | 2/8 (25%) | 8/8 (100%) | 1/9 (11%) |
| 7* | Busulfan 2 weeks | — | — | — | — |
| 8 | Busulfan 2 weeks | — | 6/6 (100%) | — | 1/8 (12%) |
| 9 | Busulfan 2 weeks | — | 8/8 (100%) | — | 3/10 (30%) |
| 10** | none | 2/5 (40%) | 5/6 (83%) | — | — |
| 11 | none | 3/7 (43%) | 7/8 (88%) | — | 0/6 (0%) |

*Mouse No. 7 died immediately after surgery;
**Mouse No. 10 died 17 weeks after surgery.

Figure 3:
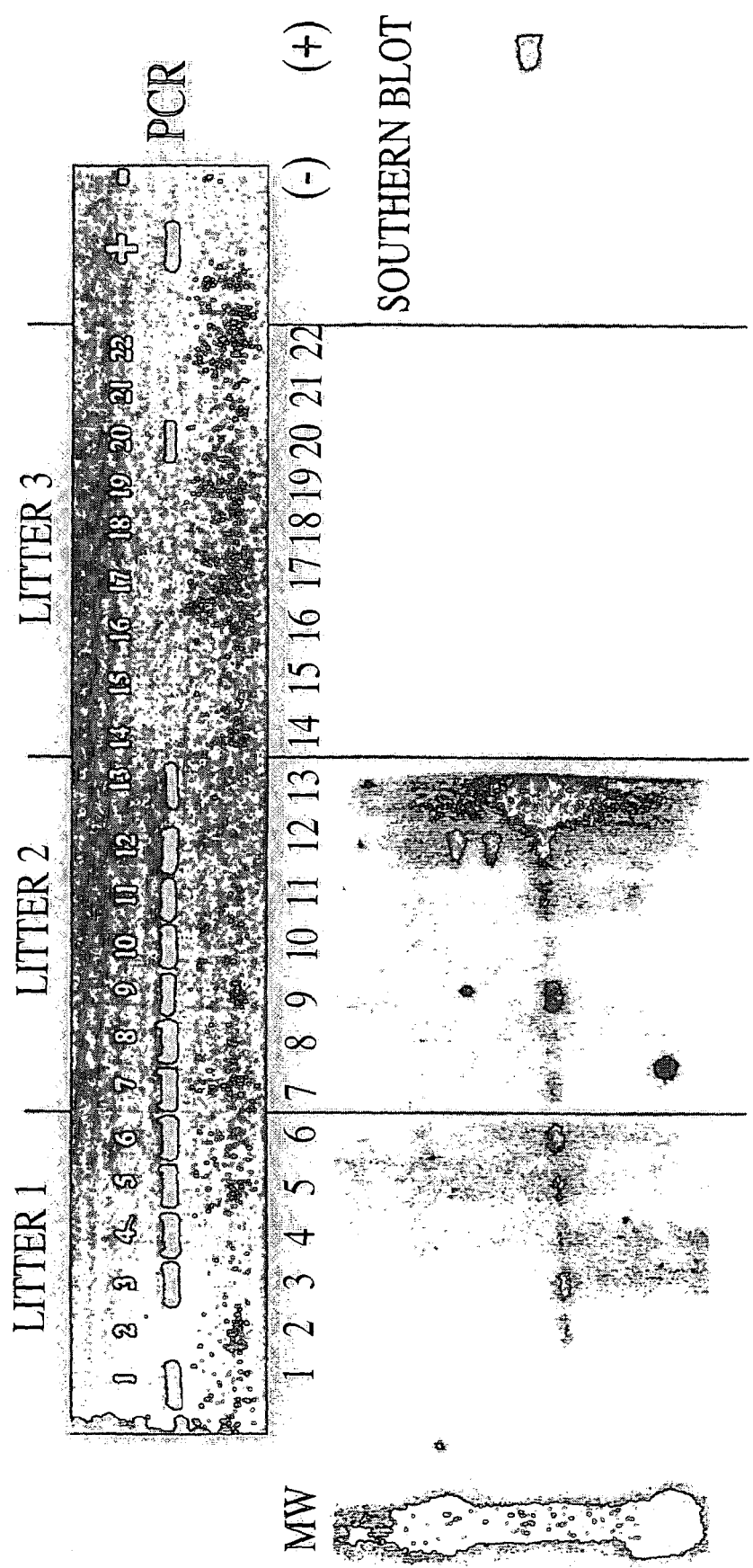
FIG. 3 shows a DNA analysis from three consecutive litters of progeny from one male treated in accordance with the in vivo method of incorporating exogenous genetic material into the genome of a vertebrate. The top panel shows GFP-specific PCR amplification products separated on an agarose gel from embryonic DNA of 22 individual progeny. In this run, there was an absence of amplification from fetus No. 2, but other PCR assays confirmed the presence of the transgenic reporter gene. The bottom panel shows a Southern blot analysis of the same DNA. The Southern blot was probed with a radiolabed GFP DNA fragment.

PCR and Southern blot analysis of DNA from embryonic offspring. Embryos at approximately embryonic day 12.5, were screened for presence of the transgene by polymerase chain reaction (PCR) and Southern blot analysis. For the PCR, GFP specific primers were used and a radiolabeled GFP cDNA probe was used for the Southern blot analysis (FIG. 3). DNA was purified from embryos using the Gentra purification system. The presence of the transgene was ascertained using PCR amplification with the following GFP specific primers:

(A) forward primer: 5'-GGT GAG CAA GGG CGA GGA GCT-3' (SEQ. ID. NO.: 1)

(B) reverse primer: 5'-TCG GGC ATG GCG GAC TTG AAG A-3' (SEQ. ID. NO.:2)

The PCR cycling conditions were: denaturing 94° C. for 1 minute, annealing at 60° C. for 1 minute and extension at 72° C. for 3 minutes. PCR ran for 35 cycles and yielded a specific GFP product 470 base pairs in length. Each cycle step can be reduced to one second—"one second PCR" to yield a distinct 470-bp PCR amplification product. Southern blot analysis was also done on the same embryo DNA extracts. The DNA was cut with BamHI-XhoI, run on a 0.8% agarose gel and blotted overnight in 20×SSC onto Hydrobond XL paper. The blots were hybridised overnight at 65° C. with a $^{32}$P-radiolabeled BamHI-XhoI GFP fragment isolated from the pHR' plasmid. The blots were washed at 65° C. (30 minutes) each in 2×SSC with 0.1% SDS, 1×SSC with 0.1% SDS, 0.1×SSC with 0.1% SDS and exposed to X-ray film.

PCR and Southern analysis showed that a high percentage of transgenic offspring were obtained in litters conceived within 15 weeks. The results are summarized in Table 3. By 20 weeks the percentage of transgenic progeny had dropped in all of the treatment groups, implying that the self-renewing spermatogonia were not transduced, but rather a population of differentiating spermatogonia. Once the daughter cells from this population had matured and left the testis they were not renewed (Huckins, C. & Oakberg, W. F. [1978]). In Table 3, the ratios are the number of transgenic offspring out of the total number of embryos in the litter.

Although pre-treatment with busulfan enhanced the transduction of spermatogonia, mice untreated with busulfan also generated transgenic offspring. Male germ cells take 60 days to differentiate from spermatogonia (Russell, L. D., et al. In: *Histological and Histopathological evaluation of the testis*, Cache River Press [1990]), undergo meiosis and form spermatozoa. Since conception was more than 60 days after transduction, it is presumed that the transgenic offspring were conceived from differentiated daughter cells of transduced spermatogonia. EGFP expression was driven by the CMV promoter and was evident in the testicular cells of the founder males 24 days after infection. The animals that were infected did not appear to have toxic side effects (Verma, I. M. and Somia, N. [1997]) with the possible exception of one dying 17 weeks after surgery.

The foregoing examples being illustrative but not an exhaustive description of the embodiments of the present invention, the following claims are presented.

We claim:

1. An in vivo method of incorporating exogenous genetic material into the genome of a mouse, said method comprising the steps of:

(a) injecting into a vas efferens, or retes of a testis of a male mouse a gene delivery mixture comprising a retroviral vector comprises at least one optionally a gene encoding a genetic selection marker, operatively linked to a promoter sequence that a transcriptional unit is formed, under conditions effective to reach within the testis of a male germ cell selected from the group consisting of spermatogonial stem cells, type B spermatogonial, primary spermatocytes, preleptotene spermatocytes, leptotene spermatocytes, zygotene spermatocytes, pachytene spermatocytes, secondary spermatocytes, secondary spermatocytes, spermatids, and spermatozoa;

(b) allowing the polynucleotide encoding a desired gene product to be incorporated into the genome of the male germ cell, so that a genetically modified male gamete is produced by the male mouse; and (c) breeding the male mouse with a female mouse, such that the genetically modified gametes is united with a female gamete and a transgenic progeny is produced thereby, that carries the polynucleotide encoding the desired gene product in its somatic cells.

2. The method of claim 1, wherein the retroviral vector is selected from the group consisting of Moloney murine leukemia virus vectors and pseudotyped lentiviral vectors.

3. The method of claim 1, wherein the retroviral vector is a lentiviral vector.

4. The method of claim 1, wherein the retroviral vector is a pseudotyped Moloney murine leukemia virus vector.

5. The method of claim 1, wherein breeding is accomplished by natural mating of the male mouse and female mouse.

6. The method of claim 1, wherein the retroviral vector further comprises a gene encoding a genetic selection marker operatively linked to a male germ cell-specific promoter.

7. The method of claim 1, wherein breeding is accomplished by artificial insemination of the female mouse with semen comprising the genetically modified male gamete.

8. The method of claim 1, wherein breeding is accomplished by in vitro fertilization of an ovum of the female mouse with the genetically modified male gamete.

9. The method of claim 1, wherein breeding is accomplished by intracytoplasmic sperm injection, subzonal insemination, or partial zona dissection, resulting in fertilization of an ovum of the female mouse with the genetically modified male gamete.

10. The method of claim 1, wherein the polynucleotide encoding a desired gene product is operatively linked to a constitutive promoter.

11. The method of claim 1, wherein the polynucleotide encoding a desired gene product is operatively linked to a cytokine-inducible promoter.

12. The method of claim 1, wherein the polynucleotide encoding a desired gene product is operatively linked to a tissue-specific promoter.

13. The method of claim 1, wherein the polynucleotide encoding a desired gene product is operatively linked to a developmentally or temporally regulated promoter.

14. The method of claim 1, wherein the polynucleotide comprises a gene encoding a genetic selection marker, and said gene is operatively linked to a constitutive promoter.

15. The method of claim 1, wherein the polynucleotide encoding a desired gene product is operatively linked to an exogenously inducible promoter.

16. The method of claim 1, wherein the polynucleotide comprises a gene encoding a genetic selection marker, and said gene is operatively linked to a tissue-specific promoter.

17. The method of claim 1, wherein the polynucleotide comprises a gene encoding a genetic selection marker, and said gene is operatively linked to a developmentally or temporally regulated promoter.

18. The method of claim 1, wherein the polynucleotide encoding the desired gene product encodes a human gene product.

19. The method of claim 1, wherein the genetic selection marker is a fluorescent protein or light-emitting protein.

20. The method of claim 1, wherein the gene delivery mixture is injected into the vas efferens of the testis.

21. The method of claim 1, wherein the gene delivery mixture is injected into the rete of the testis.

* * * * *

SEQUENCE LISTING

```
<160> NUMBER OF SEQ ID NOS:  2

<210> SEQ ID NO 1
<211> LENGTH: 21
<212> TYPE: DNA
<213> ORGANISM: Artificial Sequence
<220> FEATURE:
<223> OTHER INFORMATION: Specific primer for green fluorescent protein
      (GFP)

<400> SEQUENCE: 1
ggtgagcaag ggcgaggagc t                                              21

<210> SEQ ID NO 2
<211> LENGTH: 22
<212> TYPE: DNA
<213> ORGANISM: Artificial Sequence
<220> FEATURE:
<223> OTHER INFORMATION: Specific primer for green fluorescent protein
      (GFP)

<400> SEQUENCE: 2
tcgggcatgg cggacttgaa ga                                             22
```